(12) United States Patent
Boeke et al.

(10) Patent No.: US 6,183,964 B1
(45) Date of Patent: Feb. 6, 2001

(54) METHOD FOR IDENTIFYING SUPPRESSOR MUTATIONS FOR COMMON P53 CANCER MUTATIONS

(75) Inventors: Jef D. Boeke; Rainer K. Brachmann, both of Baltimore, MD (US)

(73) Assignee: The Johns Hopkins University, Baltimore, MD (US)

( * ) Notice: Under 35 U.S.C. 154(b), the term of this patent shall be extended for 0 days.

(21) Appl. No.: 09/184,073

(22) Filed: Nov. 2, 1998

Related U.S. Application Data

(60) Division of application No. 08/795,006, filed on Feb. 5, 1997, now Pat. No. 5,840,579, which is a continuation-in-part of application No. 08/650,125, filed on May 1, 1996, now Pat. No. 5,830,751.

(51) Int. Cl.[7] ............................... C12Q 1/68; C12N 1/19
(52) U.S. Cl. ........................... 435/6; 435/255.1; 536/23.1
(58) Field of Search ..................... 536/23.1; 435/325, 435/254.2, 320.1, 69.1, 6, 255.1

(56) References Cited

PUBLICATIONS

Waterman et al. "An Engineered Four–Stranded Coiled Coil Substitutes for the Tetrameriazation Domain of Wild–Type p53 and Alleviates Transdominant Inhibition by Tumor–derived p53 mutants" Cancer Research, Jan. 1996, vol. 56, pp. 158–163.*

Hainaut et al. "The tumor suppressor protein p53: a receptor to genotoxic stress that controls cell growth and survival" Current Opinion in Oncology. vol. 7, 1995, pp. 76–82.*

Scharer et al. "Mammalian p53 can function as a transcription factor in yeast" Nucleic Acids Research. vol. 20, No. 7, 1992, pp. 1539–1545.*

Wieczorek et al., "Structure–Based Rescue of Common Tumor–Derived p53 Mutants", *Nature Medicine* 2(10):1143–1146 (1996).

Freeman et al., "Mutation of Conserved Domain II Alters the Sequence Specificity of DNA Binding by the p53 Protein", *EMBO Journal* 13(22):5393–5400 (1994).

Buchman et al. 1988 Gene 70:245–252.

Nigro et al. 1989 Nature 342:705–708.

* cited by examiner

*Primary Examiner*—Lisa B. Arthur
*Assistant Examiner*—Jeanine Enewold
(74) *Attorney, Agent, or Firm*—Banner & Witcoff, Ltd.

(57) ABSTRACT

Intragenic suppressor mutations of common p53 mutations are able to function in cis and/or trans. These mutations are useful for identifying small molecule drugs which function in a similar fashion. In addition, the mutations themselves may be useful therapeutically, especially if they function in trans. Methods for rapidly obtaining this type of mutant employ a yeast selection system. Cells having both the negative mutation and intragenic suppressor are useful for studying the interactions of the two, in particular in determining the structure of the homotetramers and heterotetramers.

13 Claims, 10 Drawing Sheets

FIG. 2

| Hot spot regions | Codon | wild-type amino acid | mutant amino acid | | | |
|---|---|---|---|---|---|---|
| | 127 | Ser | Pro | | | |
| 132<br>\|<br>143 | 132 | Lys | Asn | | | |
| | 135 | Cys | Phe | | | |
| 151<br>\|<br>159 | 151 Pro | Pro | His | Arg | | |
| | 158 | Arg | Pro | | | |
| 172<br>\|<br>179 | 176 | Cys | Arg | | | |
| | 179 | His | Asn | | | |
| | 236 | Tyr | Asp | | | |
| 237<br>\|<br>249 | 241 Ser | Ser | Phe | | | |
| | 242 Cys | Cys | Phe | | | |
| | 244 | Gly | Asp | Ser | | |
| | 245 Gly | Gly | Ser | Arg | Ser | Ser | Asp |
| | 246 | Met | Arg | Ile | | |
| | 248 Arg | Arg | Trp | Trp | | |
| | 252 | Leu | Thr | Thr | | |
| | 257 Leu | Leu | Pro | Gln | | |
| | 259 | Asp | Tyr | | | |
| | 265 | Leu | Pro | | | |
| 272<br>\|<br>286 | 273 Arg | Arg | Pro | Pro | | |
| | 277 | Cys | Tyr | | | |
| | 278 | Pro | His | Ser | | |
| | 279 | Gly | Glu | Glu | Glu | |
| | 280 | Arg | Ser | Thr | | |
| | 281 | Asp | Gly | Tyr | Gly | |

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:1:

```
AATTTAGGCA TGTCTAGGCA TGTCTA                                      26
```

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:2:

```
AATTTAGACA TGCCTAGACA TGCCTA                                      26
```

(2) INFORMATION FOR SEQ ID NO:3:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (xi) SEQUENCE DESCRIPTION: SEQ ID NO:3:

```
GAAGGTTAAT GTGGCTGTGG TTTCAGGGTC CATAAAGCTT GTCCTGGAAG TCTCATGGAG   60
```

(2) INFORMATION FOR SEQ ID NO:4:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (xi) SEQUENCE DESCRIPTION: SEQ ID NO:4:

```
TCAGGATCCC TAGGTTCCTT TGTTACTTCT TCCG                             34
```

(2) INFORMATION FOR SEQ ID NO:5:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO:5:

```
ACCAGCAGCT CCTACACC                                               18
```

(2) INFORMATION FOR SEQ ID NO:6:

(i) SEQUENCE CHARACTERISTICS:
      (A) LENGTH: 18 base pairs
      (B) TYPE: nucleic acid
      (C) STRANDEDNESS: single (D) TOPOLOGY: linear (xi) SEQUENCE DESCRIPTION: SEQ ID NO:6:

GAGGAGCTGG TGTTGTTG                                                    18

(2) INFORMATION FOR SEQ ID NO:7:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:7:

CCATCCTCAC CATCATCAC                                                   19

(2) INFORMATION FOR SEQ ID NO:8:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:8:

GCAGGGGAGG GAGAGATGG                                                   19

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:9:

GAGGAGCCGC AGTCAGAT                                                    18

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:10:

TTTATGGCGG GAGGTAGA                                                    18

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:11:

GTTGATTCCA CACCCCCG                                                    18

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:12:

CAGTGCTCGC TTAGTGCTCC                                            20

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

AGACCCAAAA CCCAAAAT                                              18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:14:

GCCCATGCAG GAACTGTT                                              18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:15:

CATTTGCCAT CTATTGAA                                              18

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:16:

TTGTTGAGGG CAGGGGAGT                                             19

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

CATGCAGGAA CTGTAACACA TGTAGTTGTA GTGGAT                          36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:18:

CACTACAACT ACATGTGTTA CAGTTCCTGC ATGGGC                                    36

(2) INFORMATION FOR SEQ ID NO:19:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:19:

GCCGCCCATG CAGGAATTGT TACACATGTA GTTGTAG                                   37

(2) INFORMATION FOR SEQ ID NO:20:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:20:

CAACTACATG TGTAACAATT CCTGCATGGG CGGCATG                                   37

(2) INFORMATION FOR SEQ ID NO:21:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (xi) SEQUENCE DESCRIPTION: SEQ ID NO:21:

GGATTCCTCC AAAATGATTT CCACCAATTC TGCCCTCACA GCTCTGGCTT GCAGAATTTT      60

CCACCCCAAA ATGTTAGTAT CTACGGCACC AGGTCGGCGA GAATCCTGAC TCTGCACCCT     120

CCTCCCCAAC TCCATTTCCT TTGCTTCCTC CGGCAGGCGG ATTACTTGCC CTTACTTGTC     180

ATGGCGACTG TCCAGCTTTG TGCCAGGAGC CTCGCAGGGG TTGATGGGAT TGGGGTTTTC     240

CCCTCCCATG TGCTCAAGAC TGGCGCTAAA AGTTTTGAGC TTCTCAAAAG TCTAGAGCCA     300

CCGTCCAGGG AGCAGGTAGC TGCTGGGCTC CGGGGACACT TTGCGTTCGG GCTGGGAGCG     360

TGCTTTCCAC GACGGTGACA CGCTTCCCTG GATTGGGTAA GCTCCTGACT GA             412

(2) INFORMATION FOR SEQ ID NO:22:

(i) SEQUENCE CHARACTERISTICS:
        (A) LENGTH: 133 base pairs
        (B) TYPE: nucleic acid
        (C) STRANDEDNESS: single
        (D) TOPOLOGY: linear (xi) SEQUENCE DESCRIPTION: SEQ ID NO:22:

TGGATCCTCT TGCAGCAGCC AGACTGCCTT CCGGGTCACT GCCATGGAGG AGCCGCAGTC      60

AGATCCTAGC GTCGAGCCCC CTCTGAGTCA GGAAACATTT TCAGACCTAT GGAAACTGTG     120

AGTGGATCCA TTG                                                        133

(2) INFORMATION FOR SEQ ID NO:23:

(i) SEQUENCE CHARACTERISTICS:
        (A) LENGTH: 52 base pairs
        (B) TYPE: nucleic acid
        (C) STRANDEDNESS: single (D) TOPOLOGY: linear (xi) SEQUENCE DESCRIPTION: SEQ ID NO:23:

GCTCTTGACT TCAGACTTC CTGAAAACAA CGTTCTGGTA AGGACAAGGG TT            52

(2) INFORMATION FOR SEQ ID NO:24:

(i) SEQUENCE CHARACTERISTICS:
        (A) LENGTH: 311 base pairs
        (B) TYPE: nucleic acid
        (C) STRANDEDNESS: single
        (D) TOPOLOGY: linear (xi) SEQUENCE DESCRIPTION: SEQ ID NO:24:

TTTTCACCCA TCTACAGTCC CCCTTGCCGT CCCAAGCAAT GGATGATTTG ATGCTGTCCC    60

CGGACGATAT TGAACAATGG TTCACTGAAG ACCCAGGTCC AGATGAAGCT CCCAGAATGC   120

CAGAGGCTGC TCCCCCCGTG GCCCCTGCAC CAGCAGCTCC TACACCGGCG GCCCCTGCAC   180

CAGCCCCCTC CTGGCCCCTG TCATCTTCTG TCCCTTCCCA GAAAACCTAC CAGGGCAGCT   240

ACGGTTTCCG TCTGGGCTTC TTGCATTCTG GGACAGCCAA GTCTGTGACT TGCACGGTCA   300

GTTGCCCTGA G                                                       311

(2) INFORMATION FOR SEQ ID NO:25:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (xi) SEQUENCE DESCRIPTION: SEQ ID NO:25:

TTCCTCTTCC TGCAGTACTC CCCTGCCCTC AACAAGATGT TTTGCCAACT GGCCAAGACC    60

TGCCCTGTGC AGCTGTGGGT TGATTCCACA CCCCCGCCCG GCACCCGCGT CCGCGCCATG   120

GCCATCTACA AGCAGTCACA GCACATGACG GAGGTTGTGA GGCGCTGCCC CCACCATGAG   180

CGCTGCTCAG ATAGCGATGG TGAGCAGCTG GGGC                              214

(2) INFORMATION FOR SEQ ID NO:26:

(i) SEQUENCE CHARACTERISTICS:
        (A) LENGTH: 144 base pairs
        (B) TYPE: nucleic acid
        (C) STRANDEDNESS: single
        (D) TOPOLOGY: linear (xi) SEQUENCE DESCRIPTION: SEQ ID NO:26:

CACTGATTGC TCTTAGGTCT GGCCCCTCCT CAGCATCTTA TCCGAGTGGA AGGAAATTTG    60

CGTGTGGAGT ATTTGGATGA CAGAAACACT TTTCGACATA GTGTGGTGGT GCCCTATGAG   120

CCGCCTGAGG TCTGGTTTGC AACT                                         144

(2) INFORMATION FOR SEQ ID NO:27:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (xi) SEQUENCE DESCRIPTION: SEQ ID NO:27:

GTGTTGTCTC CTAGGTTGGC TCTGACTGTA CCACCATCCA CTACAACTAC ATGTGTAACA    60

GTTCCTGCAT GGGCGGCATG AACCGGAGGC CCATCCTCAC CATCATCACA CTGGAAGACT   120

```
CCAGGTCAGG AGCCACTTG                                                 139
```

(2) INFORMATION FOR SEQ ID NO:28:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (xi) SEQUENCE DESCRIPTION: SEQ ID NO:28:

```
CCTATCCTGA GTAGTGGTAA TCTACTGGGA CGGAACAGCT TTGAGGTGCG TGTTTGTGCC     60

TGTCCTGGGA GAGACCGGCG CACAGAGGAA GAGAATCTCC GCAAGAAAGG GGAGCCTCAC    120

CACGAGCTGC CCCCAGGGAG CACTAAGCGA GGTAAGCAAG CAGGAC                   166
```

(2) INFORMATION FOR SEQ ID NO:29:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (xi) SEQUENCE DESCRIPTION: SEQ ID NO:29:

```
TTGCCTCTTT CCTAGCACTG CCCAACAACA CCAGCTCCTC TCCCCAGCCA AGAAGAAAC      60

CACTGGATGG AGAATATTTC ACCCTTCAGG TACTAAGTCT TGGG                     104
```

(2) INFORMATION FOR SEQ ID NO:30:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (xi) SEQUENCE DESCRIPTION: SEQ ID NO:30:

```
CTCTGTTGCT GCAGATCCGT GGGCGTGAGC GCTTCGAGAT GTTCCGAGAG CTGAATGAGG     60

CCTTGGAACT CAAGGATGCC CAGGCTGGGA AGGAGCCAGG GGGGAGCAGG GCTCACTCCA    120

GGTGAGTGAC CTCAGC                                                    136
```

(2) INFORMATION FOR SEQ ID NO:31:

(i) SEQUENCE CHARACTERISTICS:
        (A) LENGTH: 1316 base pairs
        (B) TYPE: nucleic acid
        (C) STRANDEDNESS: single
        (D) TOPOLOGY: linear (xi) SEQUENCE DESCRIPTION: SEQ ID NO:31:

```
GCTTCTGTCT CCTACAGCCA CCTGAAGTCC AAAAAGGGTC AGTCTACCTC CCGCCATAAA     60

AAACTCATGT TCAAGACAGA AGGGCCTGAC TCAGACTGAC ATTCTCCACT TCTTGTTCCC    120

CACTGACAGC CTCCCTCCCC CATCTCTCCC TCCCCTGCCA TTTTGGGTTT TGGGTCTTTG    180

AACCCTTGCT TGCAATAGGT GTGCGTCAGA AGCACCCAGG ACTTCCATTT GCTTTGTCCC    240

GGGGCTCCAC TGAACAAGTT GGCCTGCACT GGTGTTTTGT TGTGGGGAGG AGGATGGGGA    300

GTAGGACATA CCAGCTTAGA TTTTAAGGTT TTTACTGTGA GGGATGTTTG GGAGATGTAA    360

GAAATGTTCT TGCAGTTAAG GGTTAGTTTA CAATCAGCCA CATTCTAGGT AGGGGCCCAC    420

TTCACCGTAC TAACCAGGGA AGCTGTCCCT CATGTTGAAT TTTCTCTAAC TTCAAGGCCC    480
```

-continued

```
ATATCTGTGA AATGCTGGCA TTTGCACCTA CCTCACAGAG TGCATTGTGA GGGTTAATGA    540

AATAATGTAC ATCTGGCCTT GAAACCACCT TTTATTACAT GGGGTCTAAA ACTTGACCCC    600

CTTGAGGGTG CCTGTTCCCT CTCCCTCTCC CTGTTGGCTG GTGGGTTGGT AGTTTCTACA    660

GTTGGGCAGC TGGTTAGGTA GAGGGAGTTG TCAAGTCTTG CTGGCCCAGC CAAACCCTGT    720

CTGACAACCT CTTGGTCCAC CTTAGTACCT AAAAGGAAAT CTCACCCCAT CCCACACCCT    780

GGAGGATTTC ATCTCTTGTA TATGATGATC TGGATCCACC AAGACTTGTT TTATGCTCAG    840

GGTCAATTTC TTTTTTCTTT TTTTTTTTTT TTTTTCTTTT TCTTTGAGAC TGGGTCTCGC    900

TTTGTTGCCC AGGCTGGAGT GGAGTGGCGT GATCTTGGCT TACTGCAGCC TTTGCCTCCC    960

CGGCTCGAGC AGTCCTGCCT CAGCCTCCGG AGTAGCTGGG ACCACAGGTT CATGCCACCA   1020

TGGCCAGCCA ACTTTTGCAT GTTTTGTAGA GATGGGGTCT CACAGTGTTG CCCAGGCTGG   1080

TCTCAAACTC CTGGGCTCAG GCGATCCACC TGTCTCAGCC TCCCAGAGTG CTGGGATTAC   1140

AATTGTGAGC CACCACGTCC AGCTGGAAGG GTCAACATCT TTTACATTCT GCAAGCACAT   1200

CTGCATTTTC ACCCCACCCT TCCCCTCCTT CTCCCTTTTT ATATCCCATT TTTATATCGA   1260

TCTCTTATTT TACAATAAAA CTTTGCTGCC ACCTGTGTGT CTGAGGGGTG AACGCC       1316
```

(2) INFORMATION FOR SEQ ID NO:32:

(i) SEQUENCE CHARACTERISTICS:
        (A) LENGTH: 393 amino acids
        (B) TYPE: amino acid
        (C) STRANDEDNESS: single
        (D) TOPOLOGY: linear (xi) SEQUENCE DESCRIPTION: SEQ ID NO:32:

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
```

```
                   210                 215                 220
Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

METHOD FOR IDENTIFYING SUPPRESSOR MUTATIONS FOR COMMON P53 CANCER MUTATIONS

This application is a divisional application of U.S. Ser. No. 08/795,006, filed Feb. 5, 1997, now U.S. Pat. No. 5,840,579, which is a continuation-in-part of Ser. No. 08/650,125 filed May 1, 1996 now U.S. Pat. No. 5,830,751.

The U.S. Government has a paid-up license in this invention and the right in limited circumstances to require the patent owner to license others on reasonable terms as provided for by the terms of grants awarded by the National Institutes of Health.

BACKGROUND OF THE INVENTION

More than half of all human cancers are associated with one or more alterations in the tumor suppressor gene TP53 (1–4). Many premalignant lesions, a subset of malignant clones, and germlines of families prone to cancer are characterized by the presence of one wild-type and one mutant allele of 2P53 (5–9) (See SEQ ID NO:21–32). In this situation the mutant p53 protein may act in a dominant-negative fashion, ultimately leading to loss of heterozygosity and thus a further growth advantage for the malignant cells. Alternatively, the mutant p53 protein may have acquired a new tumor promoting act which is independent of wild-type p53. These hypotheses are based on the analysis of only a few TP53 mutations usually in the setting of overexpression of the mutant protein, and their relevance to TP53 mutations in general has not been proven (8, 10–13).

Absent or significantly reduced activity of the tumor suppressor protein p53 can be due to the presence of abnormally high levels of host proteins, i.e. mdm-2 or viral proteins, i.e. high-risk human papilloma virus E6 (8, 11, 35). However, in the majority of cancers p53 inactivation is caused by missense mutations in one TP53 allele with concomitant loss-of-heterozygosity (8, 10–12, 36. The missense mutations can be further classified into those affecting codons important for contacting the DNA binding sites and structural mutants affecting codons which stabilize the hydrophobic p53 core domain (31–33, 37). The unusually high frequency of TP53 missense mutations in human cancers can be explained by their dominant-negative effect. Interference with the initially still present wild-type p53 allele leads to increased genetic instability, loss-of-heterozygosity and thus complete abrogation of p53 function (10, 11, 38, 39, 40). In addition, there is evidence that at least some of the same missense mutations confer a gain-of-function (35, 40).

Reconstitution of wild-type p53 activity in these cancers could be of large therapeutic benefit (41–47). The anti-tumor effect of reconstituted p53 activity could be further enhanced by utilization of conventional anti-cancer therapies (43, 44, 46). There is a need in the art for means of correcting the abnormalities found in p53 in human cancers.

SUMMARY OF THE INVENTION

It is an object of the invention to provide a human p53 cDNA which suppresses the phenotype of p53 mutations found in human cancers.

It is another object of the invention to provide human cells which carry both dominant-negative and suppressor type p53 mutations.

It is an object of the invention to provide cells which carry human p53 CDNA which suppresses the phenotype of p53 mutations found in human cancers.

It is an object of the invention to provide methods for treating cancer cells.

It is an object of the invention to provide methods for identifying mutations in a human p53 gene which suppress the phenotype of dominant-negative p53 mutations.

It is an object of the invention to provide a yeast cell useful for selecting and studying mutations in human p53.

It is another object of the invention to provide a method of identifying compensatory mutations in TP53 which suppress dominant-negative TP53 mutant phenotypes.

It is still another object of the invention to provide a method of identifying potential therapeutic agents.

It is yet another object of the invention to provide a method of screening putative carcinogens.

It is yet another object of the invention to provide a method for identifying cellular proteins which interact with p53 and abrogate its activity.

It is an object of the invention to provide a kit for isolating mutations in p53.

It is another object of the invention to provide a gene fusion useful for isolating and studying p53 mutations.

These and other objects of the invention are provided by one or more of the embodiments described below. In one embodiment of the invention a nucleic acid encoding human p53 is provided which carries at least one intragenic suppressor mutation, wherein said mutation suppresses a dominant-negative mutation of p53, and at least one dominant negative mutation of p53.

In another embodiment of the invention a nucleic acid is provided which encodes human p53. The nucleic acid comprises at least one intragenic suppressor mutation, wherein said intragenic suppressor mutation suppresses a dominant-negative mutation of p53, wherein the at least one intragenic suppressor mutation is selected from the group consisting of: T123P, N268D, N239Y, S240N, and T123A+H168R.

In another embodiment of the invention a human cell is provided which comprises:

a human p53 DNA which comprises a dominant-negative mutation; and a nucleic acid encoding human p53 which carries at least one intragenic suppressor mutation, wherein said mutation suppresses a dominant-negative mutation of p53 in trans.

In still another embodiment of the invention a method of treating cancer cells is provided. The method comprises:

introducing into the cancer cells a nucleic acid which carries at least one intragenic suppressor mutation, wherein said mutation suppresses a dominant-negative mutation of p53, whereby a neoplastic phenotype of the cancer cells is suppressed or apoptosis is induced.

In yet another embodiment of the invention a method is provided for identifying mutations in a human p53 gene which suppress the phenotype of a dominant-negative p53 mutation. The method comprises the steps of:

introducing a p53 nucleic acid which has been mutagenized into a cell which carries a dominant-negative mutation in a p53 DNA;

testing the phenotype of the cell to determine whether the cell behaves like a cell carrying a wild-type p53 or a cell carrying a dominant-negative p53 mutation; wherein a cell which behaves like a cell carrying a wild-type p53 is a cell carrying a p53 suppressor mutation on the mutagenized p53 nucleic acid.

In another embodiment of the invention a method is provided for identifying mutations in a human p53 gene which suppress the phenotype of dominant-negative p53 mutations. The method comprises the step of:

testing the phenotype of a cell which comprises a p53 nucleic acid which carries a dominant-negative mutation and which has been mutagenized, to determine whether the cell behaves like a cell carrying a wild-type p53 or a cell carrying a dominant-negative p53 mutation; wherein a cell which behaves like a cell carrying a wild-type p53 is a cell carrying a p53 suppressor mutation on the mutagenized p53 nucleic acid.

In one embodiment of the invention a yeast cell is provided. The cell comprises a first reporter gene which is selectable or counterselectable. The reporter gene is operably linked to a DNA sequence to which human p53 specifically binds. The cell also comprises a first fusion gene which expresses a human p53 in the cell. The fusion gene comprises a yeast promoter operably linked to a human p53 coding sequence.

In another embodiment of the invention a method of identifying compensatory mutations in TP53 which suppress dominant-negative 7P53 mutant phenotypes is provided. The method involves providing a cell which comprises:

a reporter gene which is selectable, wherein the reporter gene is operably linked to a DNA sequence to which human p53 specifically binds; and a first fusion gene which expresses a dominant-negative allele of human p53 in the cell, the fusion gene comprising a promoter operably linked to a human p53 coding sequence.

Then a population of DNA molecules comprising a second fusion gene is introduced into the cell. The second fusion gene comprises a promoter operably linked to a mutagenized human p53 coding sequence. Phenotypic revertants of the dominant-negative allele of human TP53 are selected using the selectable phenotype of the reporter gene.

According to another embodiment of the invention a method of identifying potential therapeutic agents is provided. A cell is provided which comprises:

a reporter gene which is selectable, wherein the reporter gene is operably inked to a DNA sequence to which human p53 specifically binds; and a fusion gene which-expresses a dominant-negative allele of human 7P53 in the cell, the fusion gene comprising a promoter operably linked to a human p53 coding sequence.

Test, compounds are contacted with the cell. The selectable phenotype of the reporter gene, is assayed. Desirable test compounds are identified as potential therapeutic agents if they induce the cell to display the selectable phenotype.

In another aspect of the invention a method of screening putative carcinogens for their effect on a p53 allele is provided. A cell is provided which comprises:

a reporter gene which is counterselectable, wherein the reporter gene is operably linked to a DNA sequence to which human p53 specifically binds; and a fusion gene which expresses human p53 in the cell, the fusion gene comprising a promoter operably linked to a human p53 coding sequence.

The cell is contacted with a putative carcinogen. Cells are isolated which contain a mutation in the human p53 coding sequence by counterselecting for loss of expression of the reporter gene.

According to another embodiment of the invention cellular proteins which interact with p53 and abrogate its activity are identified A population of cells is provided which comprise:

a reporter gene which is counterselectable, wherein the reporter gene is operably linked to a DNA sequence to which human p53 specifically binds; and a fusion gene which expresses human p53 in the cell, the fusion gene comprising a promoter operably linked to a human p53 coding sequence.

A library of human nucleic acid molecules is introduced into the population of cells. Each of the nucleic acid molecules is operably linked to expression control sequences so that the human nucleic acid is expressed in the cell. The cells are assayed to identify those which express the counterselectable phenotype of the reporter gene. The counterselectable phenotype identifies cells which express a protein which abrogates p53 activity.

According to another aspect of the invention a kit is provided. The kit comprises three yeast strains. The first yeast strain comprises a centromeric plasmid which itself comprises: a fusion of a yeast alcohol dehydrogenase promoter operably linked to a human p53 coding sequence; and a yeast histidine (HIS3) gene. The first yeast strain also comprises an integrated reporter gene which consists of a p53 consensus binding sequence inserted upstream from the URA3 locus. The second yeast strain comprises an integrated reporter gene which consists of a p53 consensus binding sequence inserted upstream from the URA3 locus. The third yeast strain comprises a cetromeric plasmid which itself comprises a fusion of a yeast alcohol dehydrogenase promoter operably linked to a human p53 coding sequence, and a yeast L1U2 gene. The third yeast strain also contains an integrated reporter gene which consists of a p53 consensus binding sequence inserted upstream from the URA3 locus. The first strain is of a compatible mating type to the second and third strains.

In still another embodiment of the invention a tripartite gene fusion is provided. The fusion comprises a human p53-specific DNA-binding site, a yeast URA3 gene; and a portion of a yeast SPO13 gene. The human p53-specific DNA-binding site is upstream of the URA3 gene, and the portion of the-yeast SPO13 gene is interposed between the -URA3 gene and the human p53 -specific DNA-binding site. Moreover, the portion of the yeast SPO13 gene consists of the first 15 codons of SP013 and nucleotides 5' to nucleotide –170.

These and other embodiments of the invention provide the art-with tools for studying mutagenesis and carcinogenesis in general, as well as for studying the important cancer-related gene TP53.

Figure 1:
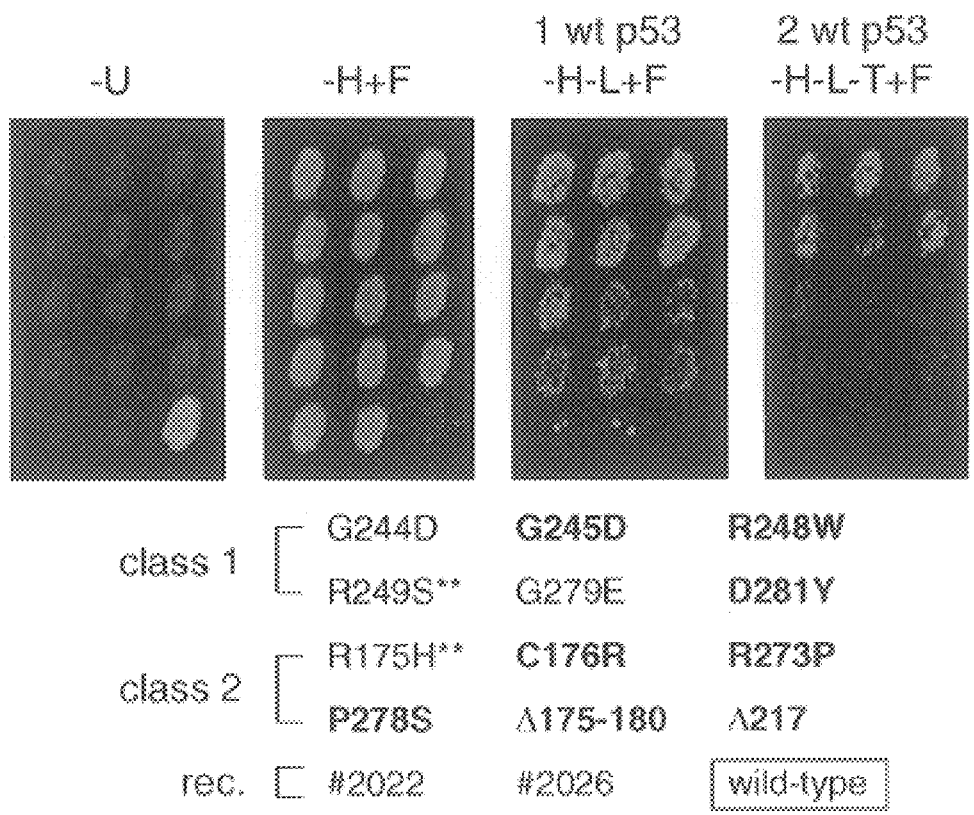
FIG. 1. Phenotypes of p53 mutants selected in yeast. In contrast, to wild-type p53 (phenotype Ura$^+$Foa$^s$) all dominant-negative as well as recessive mutants are Ura-Foa$^R$. Upon mating to strains with one or two wild-type ADH-p53 expression vectors the dominant-negative mutants can be classified by their degree of dominance over wild-type p53. The stronger class 1 interferes with one and two copies of wild-type ADH-pS3 and thus survives on Foa plates. The weaker class 2 is only dominant over one wild-type copy. For the p53 mutants in bold letters NcoI/StuI fragments with the mutations were recloned into the wild-type ADH-p53 plasmid pRB16. The mutants with ** represent hotspot codons which were not identified by our screen (1, 2, 4) (see Table 3). #2022 and #2026 are recessive mutations leading to the expression of truncated p53 proteins. The media used were SC -Ura (-U), SC -His +Foa (-H+F), SC -His -Lcu+Foa (-H-L+F), and SC -His -Leu -Trp +Foa (-H-L-T+F). The -U and -H+F media test for p53 function (wild-type grows on -U and fails to grow on -H+F). The -H-L+F medium tests for the ability of mutant p53 to interfere with the function of a single wild-type, copy of p53 (present on a LEU2.plasmid); dominant--negative mutants will grow on this medium. The -H-LT+F medium tests for the ability of mutant p53 to interfere with the function of two wild-type copies of p53 (present on LEU2 and TRP1 plasmids).

FIG. 2. Comparison of the dominant-negative ADH-p53 mutations selected in yeast to the five hotspot regions of human cancer mutations and to reported germline mutations (Li-Fraumeni syndrome and others). The boxed yeast mutations hit the hotspot regions (2, 5). For codons with shaded background germline mutations have been reported (7, 27, 28). The figure shows the clustering of the strongest dominant mutations-to codons 179, 241–248 and 277–281. Mutations of class 1 are in bold and of class 2. in plain text.

Figure 3:
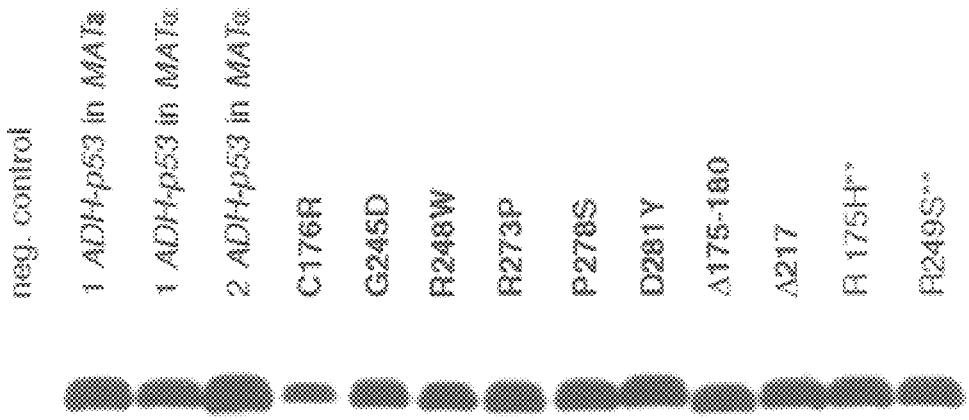

FIG. 3. Western Blot analysis with PAb 1801 (34) for p53 protein expression in yeast strains with wild-type and mutant ADH-p53 expression vectors; Protein levels for the dominant-negative mutants are similar-to that of-wild-type pS3 The yeast strain with 2 expression vectors for wild-type ADH-p53 shows approximately two-fold more p53 protein than all other strains indicating that the strongest dominant p53 mutants of class 1 can in fact override higher levels of wild-type protein. For the p53 mutants in bold letters NcoI/StuI fragments with the mutations were cloned unto wild-type ADH-p53, The mutants with ** represent hotspot codons which were not identified by our screen (1, 2, 4).

Figure 4:
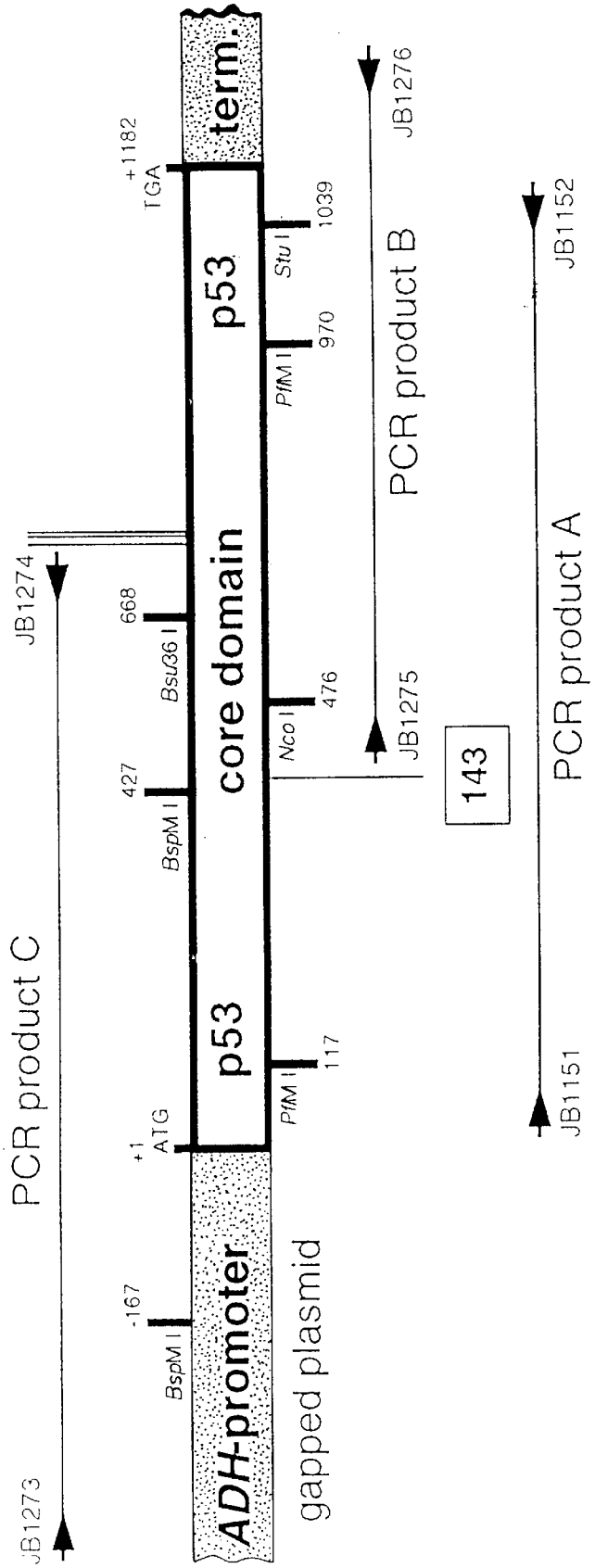

FIG. 4. Design of the PCR mutagenesis and gap repair experiments. In the first approach, the entire core domain of the p53 ORF was mutagenized for several yeast expression plasmids of common cancer missense mutations using primers JB1151 and JB1152 (PCR product A). The same plasmids were gapped with the restriction enzyme PflM I. This strategy included the original mutation in the PCR product. In the second approach, regions adjacent to the p53 mutations were PCR mutagenized with the intent to reduce reversions of the original p53 mutations that restore the wild-type amino acids. For V143A, the downstream region was PCR amplified with primers JB1275 and JB1276 (PCR product B) and the expression plasmid gapped with an Nco I/Stu I digestion. For G245D, G245S, R248W and R249S the upstream region was PCR amplified with primers JB1273 and JB1274 (PCR product C) and the expression plasmids gapped with BspM I and Bsu36 I.

Figure 5:
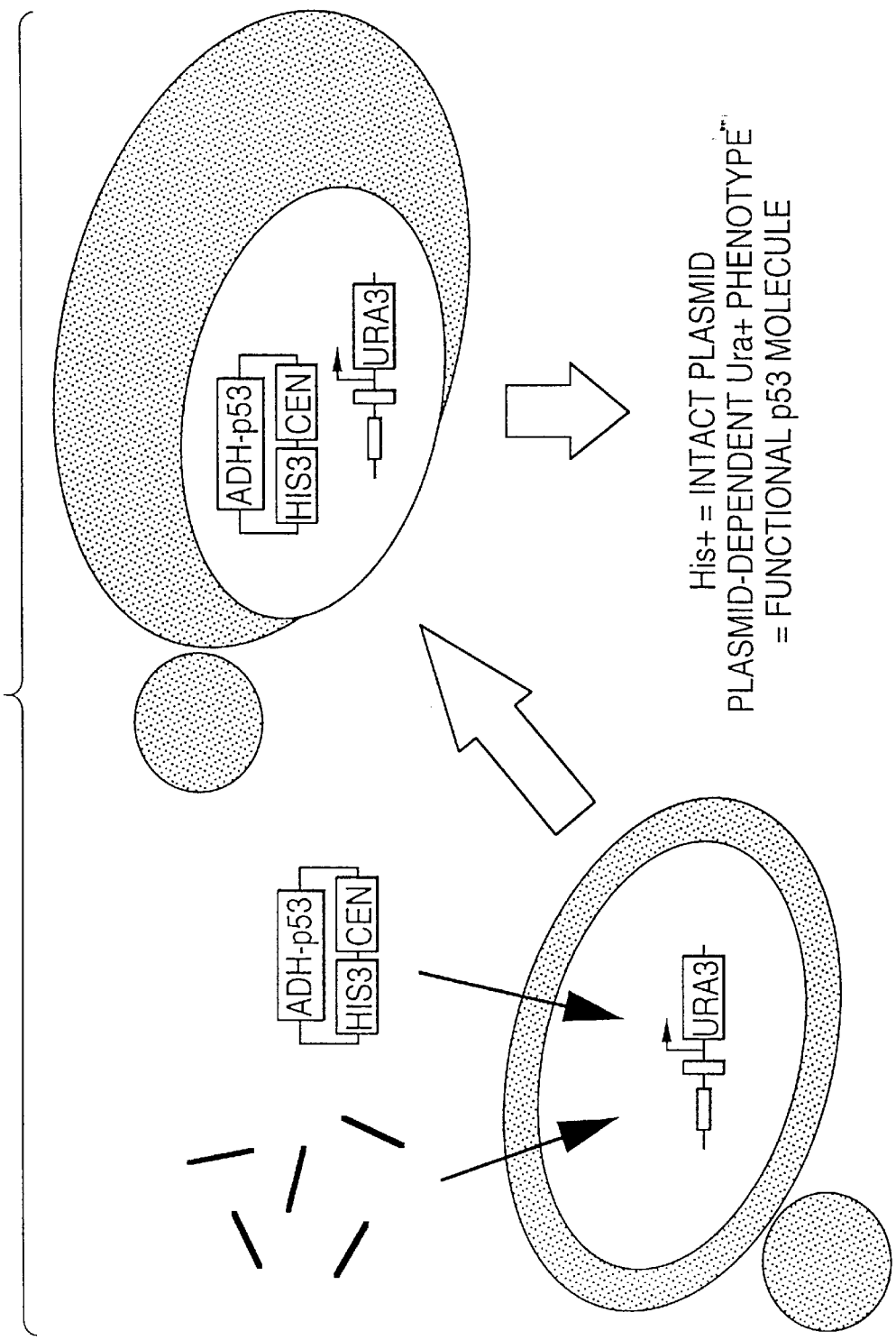

FIG. 5. Cotransformation of PCR products and gapped expression plasmids. The PCR products and gapped plasmids were designed to have overlapping areas at both ends. Thus, we could take advantage of S. cerevisiae's high efficiency homologous recombination by cotransforming the two products. The yeast transformants were evaluated for the His$^+$ phenotype, indicating a functional HIS31CEN yeast expression plasmid and a plasmid-dependent Ura$^+$ phenotype, representing expression of a functional p53 molecule, potentially containing the original p53 -missense mutation and a new second-site suppressor mutation.

Figure 6A:
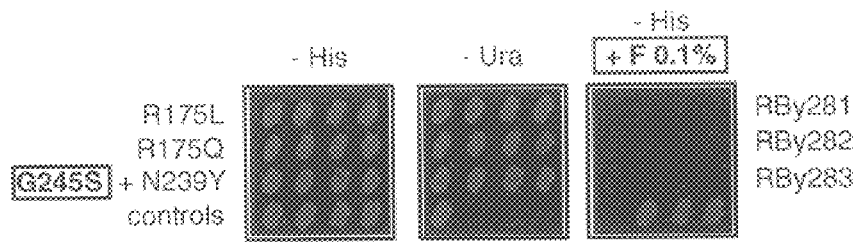
Figure 6B:
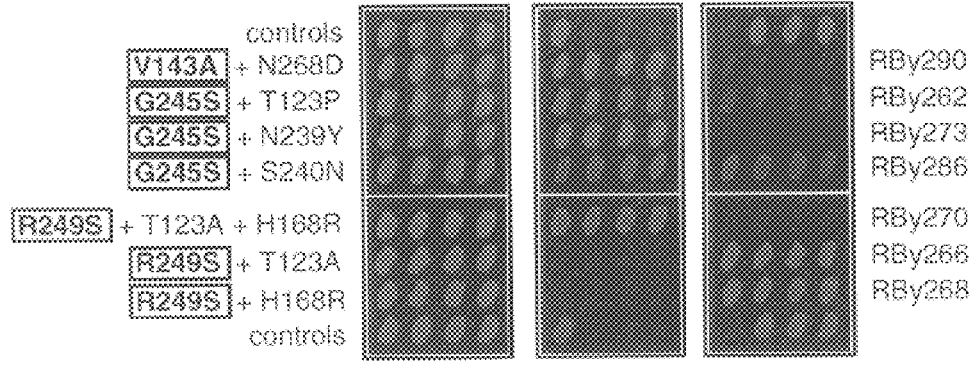

FIG. 6. Phenotypes of intracodon mutations for R175 and second-site suppressor mutations for R249S. FIG. 6A—The two subcloned intra codon mutations R175L and R175Q, as well as the second-site suppressor mutation N239Y for the cancer mutation G245S behave Mike wild-type p53 in our assay ($U^+F^s$). Controls included from left to right RBy41, RBy57, RBy234, and RBy198 (50). FIG. 6B—All subcloned suppressor- mutations showed the same phenotype as the initially isolated plasmids. V132A +N268D behaves like wild-type p53 in our assay ($U^+F^s$). For G245S, N239Y is a complete suppressor mutation ($U^+F^S$) T123P and S240N are partial suppressor mutations, since they have the phenotype $U^+F^R$. T123A+H168R completely suppress the mutant phenotype of R249S. However, neither T123A nor H168R alone show, not even partial, suppression of R249S. The controls for the upper plate were RBy41, RByS7, RBy287 (pRB255 with V143A in RBy33) and RBy198. The controls for the lower plate were RBy41, RBy55 (RB633 with pRS413 (52), RBy57 and RBy235 (pRqB214 with R249S in RBy33) (38, 50).

Figure 7:
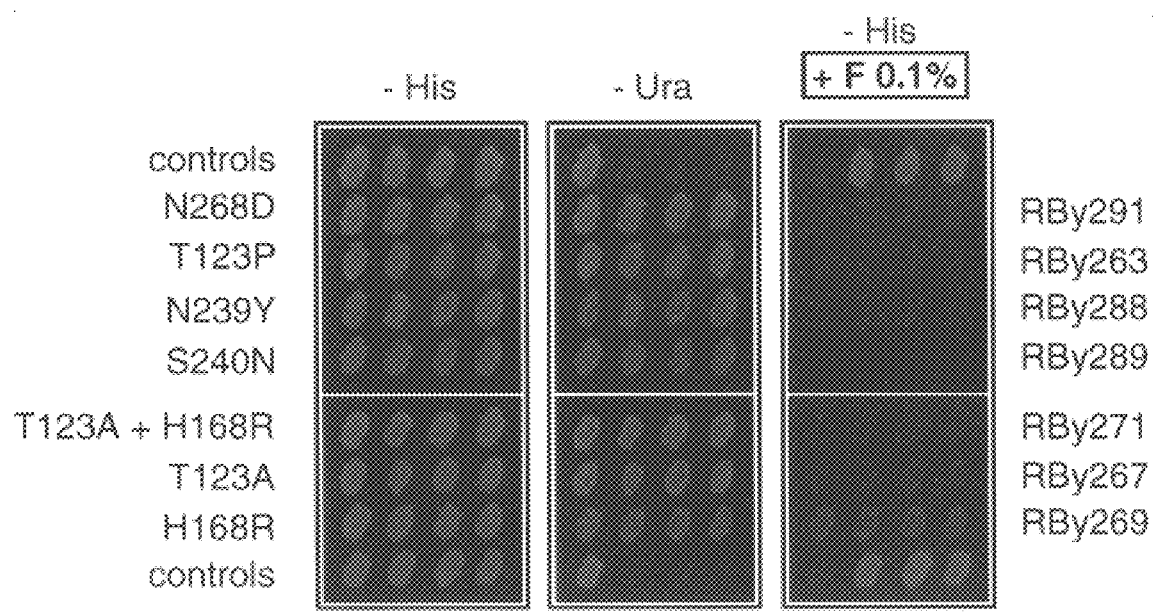

FIG. 7. Phenotypes of second-site suppressor mutations in wild-type p53 without the original cancer mutations. All second-site suppressor mutations in wild-type p53 except H168R behave like wild-type p53 in our assay. This is consistent with the fact that these missense-mutations have not been reported in the database for cancer mutations. H168R is the only missense mutation which has been reported as a cancer mutation. It shows a $U^+F^R$ phenotype indicating partial loss of wild-type p53 function. The controls for the upper and lower plate were identical to FIG. 7B.

Figure 8:
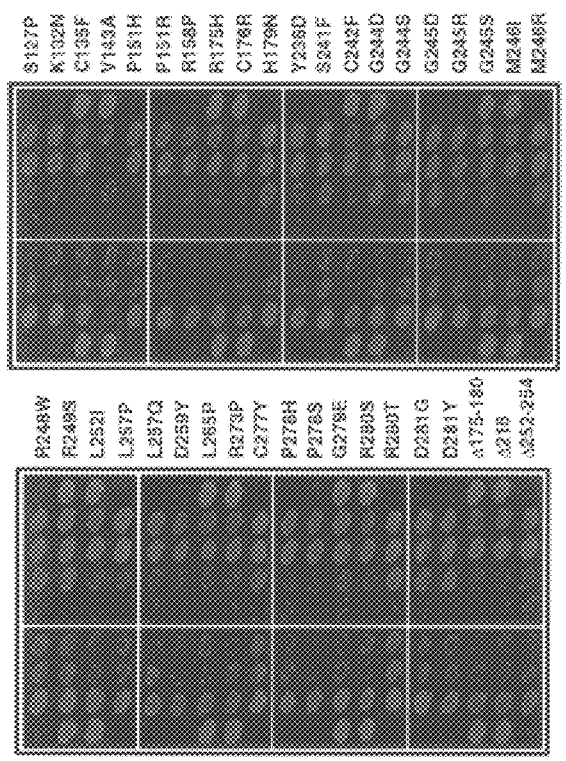

FIG. 8. Phenotypes for all identified suppressor mutations and T123A alone in trans. 37 strains expressing p53 missense mutants and 3 expressing mutants with in-frame deletions were mated to strains expressing either wild-type p53 or the indicated suppressor forms of p53. The diploids expressing both plasmids were selected for on SC -His. -Leu plates replica-plated to SC -His -Leu +Foa 0.1% plates and incubated for 2 days. As previously described wild-type p53 was recessive to the p53 mutants (38). The same was true for the T123A+H168R and the N268D form of p53. However the suppressor mutation T123P in wild-type p53 was completely immune to the dominant-negative effect of the p53 mutants resulting in a very tight Foa$^s$ phenotype. N239Y, S240N and T123A showed partial suppression of the Foa$^R$ phenotype as indicated by minimal growth of the diploids on Foa plates. After five days of incubation, T123P continued to show complete suppression of Foa resistance, while the other suppressor mutations could be classified into the two slightly stronger suppressors N239Y and S240N and the weaker suppressor T123A. The controls on all plates were diploids with, from left to right, two wild-type p53 expression plasmids and two reporter genes, two wild-type p53 expression plasmids and two URA3 knock-outs (ura3-52) and two vector controls and two reporter genes.

Figure 9:
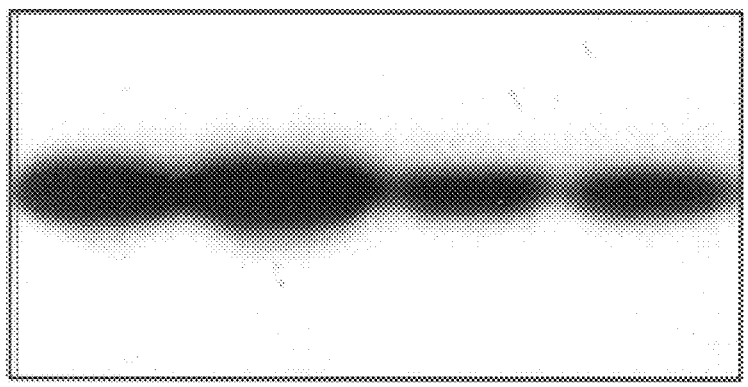

FIG. 9. Protein expression levels for wild-type p53, T123P and T123A+H168R. Anti-p53 immunoblotting showed that the immunity of T123P to the negative dominance of p53 mutants was not due to elevated protein levels. The two left lanes show strains with one and two wild-type p53 expression plasmids. The protein levels of strains with T123P and T123A+H168R were equal to or slightly less than for the strain with one wild-type plasmid.

Figure 10:
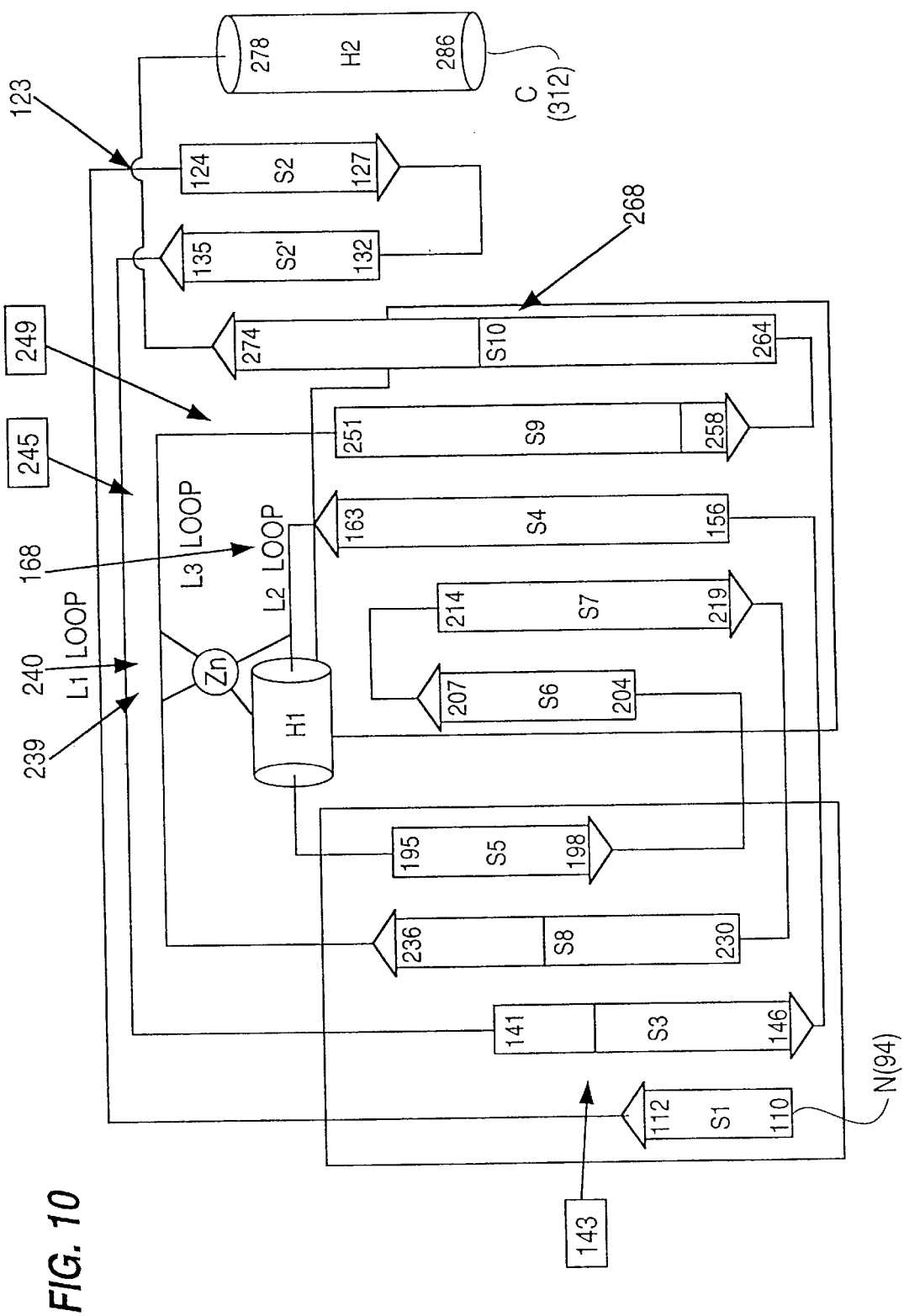

FIG. 10. Location of the original missense cancer Mutations and their second-site suppressor mutations. Both V143A and its suppressor N268D are located in the β-sandwich which acts as the scaffold for the actual DNA binding surface of the p53 core domain. G245S and R249S are located on the L3 loop which makes contact with the minor groove of p53 binding sites and also provides stability to the DNA binding surface by interactions with a Zinc atom. Two of the suppressors for G245S are also located on the L3 loop (N239Y and S240N). The third (T123P) is part of the loop-sheet-helix motif. A change of this codon (T123A) together with H168R in the I2 loop can suppress R249S. H168R is the only mutation reported as a cancer mutation. No missense mutations or in-frame deletions have been reported for the area from codon 118 to 124. For all other suppressor codons, cancer missense mutations have been found, but not those isolated by us. The topological diagram was provided by (31).

Figure 11:
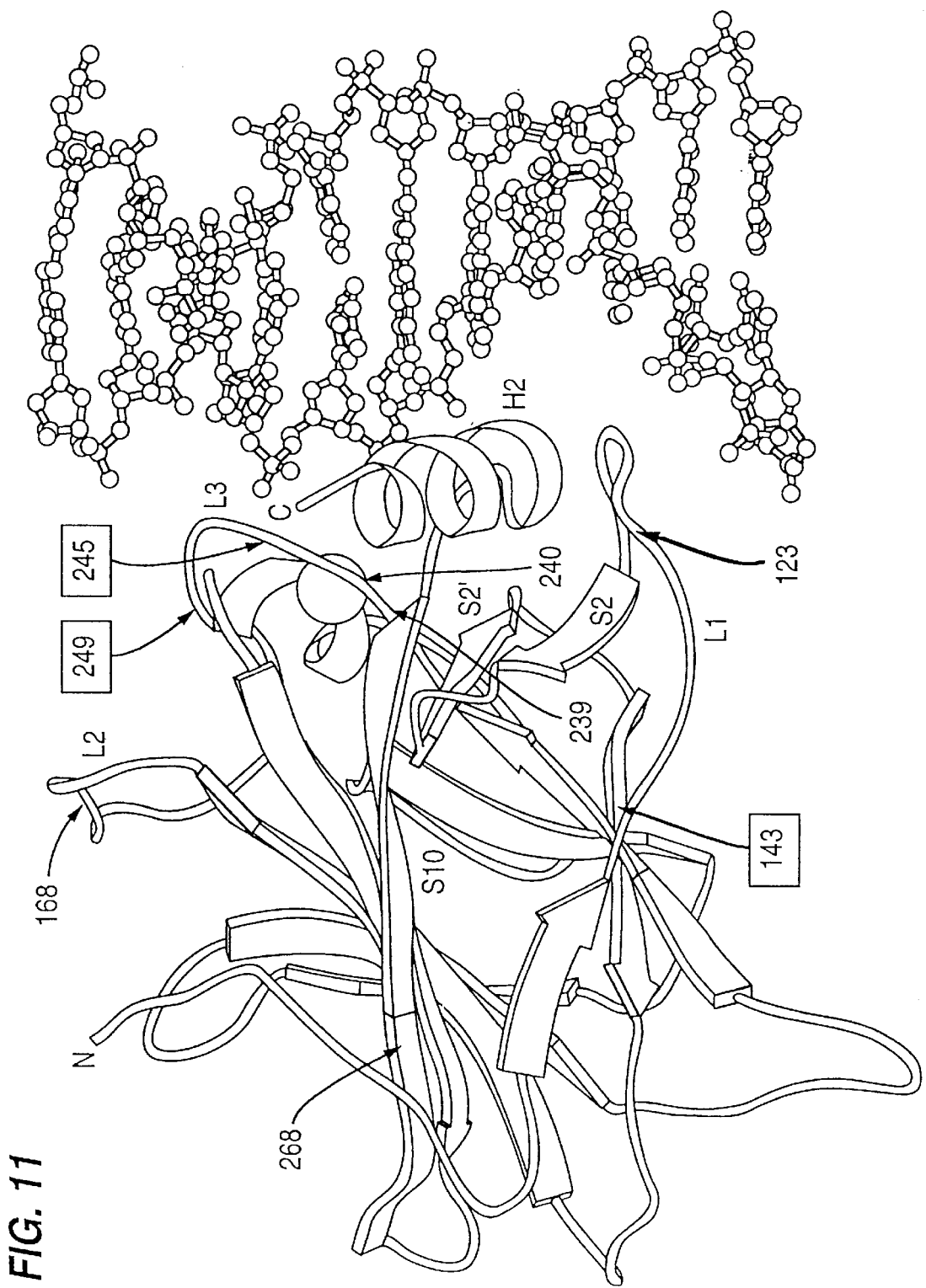

FIG. 11. Proposed mechanisms for the suppressor mutations. Based on available structural data (31) N239Y and S240N probably make new DNA contacts. T123A and T123P are close to, but not directly at the interface between DNA and p53 core domain. These two mutations may be, able to stabilize the DNA binding surface of the core domain. H168R appears to compensate directly for R249S. The first two mechanisms may represent more universal forms of suppression and hence may reverse the effects of other p53 mutations as well. N268D is the most interesting candidate for a general suppression mechanism which could be exploited for rational drug design. N268) clearly does not compensate directly for V143A,. but is predicted to make a new hydrogen bond with the backbone amide of codon 111. This may represent a general mechanism for stabilization of the hydrophobic core of p53. The sketch of the core domain-DNA complex was provided by (31).

DETAILED DESCRIPTION OF THE PREFERRED EMBODIMENTS

We developed a yeast assay for p53 and its consensus DNA binding site to screen for and analyze spontaneous dominant-negative p53 mutations. We have discovered that such mutations cluster in the mutational hotspots of human cancers. We have demonstrated different degrees of dominance, the most dominant mutations localizing to codons 179, 241–248 and 277–281. These results are fully consistent with a dominant-negative mode of action for the large majority of tumorigenic TP53 alleles.

Our p53 assay is based on the principles of yeast systems designed by Fields and others, which allow the study of protein/protein interactions by simple phenotypic readouts (19–23). The use of a counterselectable marker, such as URA3, as the reporter gene, allows screening for and against p53 expression. In a preferred embodiment, activation of URA3 leads to survival on medium lacking uracil, but prevents growth on plates containing 5-fluoro-orotic acid (Foa) due to the conversion of Foa to a toxic product (resulting in a Ura$^+$ Foa$^s$phenotype) (24). In our assays, URA3 activation depends upon the site-specific binding of p53 to its consensus DNA binding site (25) placed upstream of URA3; p53 expression is driven by the ADH1 promoter from a CEN (centromeric) plasmid (ADH-p53), which is maintained at approximately one copy per cell.

Yeast cells are employed for the assays described here, although other cell types, both prokaryotic and eukaryotic, preferably with well defined genetics, can be used as well. Yeast are particularly useful because of their well-developed genetic system. Reporter genes useful according to the present invention are selectable or counterselectable, or both. The URA3 gene is particularly useful. Other useful counterselectable genes include LYS2, LYS5, CAN1, MET2, MET15, and GAL1. The reporter gene is operably linked to a DNA sequence to which human p53 specifically binds. An actual human p53-binding sequence or any sequence which conforms to the consensus sequence taught by el-Deiry (25) can be used. Among this family of sequences there may be a slight variation in the behavior in the assays. As shown by the actual p53-binding human sequences, slight variations from the consensus sequence can be made while still enabling ps3 10 specifically bind. Operable linkage, according to the present invention, means that the DNA sequence is upstream of the reporter gene and close enough so that p53 binding activates transcription of the reporter gene. Typically this is within about 1 kb.

It is desirable that at least one of the reporter gene constructs of the present invention be integrated in the genome. This can be accomplished readily by amplification of the construct and introduction into yeast by any technique known in the art. The transformed construct can integrate via homologous recombination at the site of the endogenous reporter gene or at any marker gene site. This event can be readily selected for if the genomic target site is mutated and the transforming marker gene is wild-type.

A fusion gene which expresses a human p53 in a yeast cell typically has p53 coding sequences linked to an endogenous yeast cell promoter. Useful promoters are those for "housekeeping" genes which are typically expressed throughout the life cycle at high levels. One such useful promoter is that for the alcohol dehydrogenase gene, but others may be used as is convenient. Promoters are operably linked to a TP53 gene when they drive transcription of the gene. Such promoters are usually upstream and within about 1 kb of the start of translation.

Suitable TP53 alleles for use in the various embodiments of the present invention are wild-type alleles as well as mutants. The mutant alleles may be those which are experimentally made, but more interesting alleles ale those which are found in human cancers. Most interesting alleles are those which are dominant-negative, which means that the alleles cause a mutant phenotype even in the presence of a wild-type allele.

After generation of mutations in TP53 on a fit expression plasmid it is often desirable to test the mutant allele in the presence of wild-type TP53. This can be accomplished by mating with a compatible haploid yeast strain which contains a wild-type TP53 expression construct. Preferably the two TP53 expression constructs will produce p53 at similar levels, or if not, at levels which can be manipulated, such as by controlled induction. The phenotype of the diploid cell containing a mutant and wild-type allele of TP53 can be assayed or observed, to determine whether the mutation is recessive or dominant.

In another aspect of the invention a second reporter gene is introduced into the yeast cell which contains a reporter gene as well as a fusion gene expressing p53.The second reporter gene can be selectable, counterselectable, or both. The reporter gene can be the same or different from the first reporter gene. Like the first reporter gene, the second reporter gene is operably linked to a DNA sequence to which human p53 specifically binds. This reporter gene allows one to determine whether a mutation occurred on the TP53-plasmid or on the genomic reporter gene.

The set of yeast strains and plasmids disclosed here lend themselves to a variety of methods. In one method, mutations which are able to compensate for a dominant-negative TP53 mutation are identified. Such compensatory mutations are of intrinsic scientific interest, to determine interactions between portions of the p53 multimer. In addition, a compensatory mutation which functions in trans to suppress a dominant-negative TP53 mutant phenotype will be useful in therapeutic applications. Such mutations will also be instructive in the design of drugs which have the same effect on dominant-negative p53 mutants. By using the strains described herein, one can, for example mutagenize human p53 coding sequences and introduce them to strains which contain a selectable reporter gene operably linked to a DNA sequence to which human p53 specifically binds, and a TP53 expression construct which has a dominant-negative mutation. Desirably the mutation will be one commonly found in human tumors. Using the selectable phenotype of the reporter gene, one can select for a change in phenotype due to the introduction of a particular mutagenized human p53 coding sequence.

Several such intragenic suppressor mutations have been found. Some function in cis, and some also function in trans. Although an exhaustive study has not yet been done, the suppressor mutations do not appear to be located in the H2 a-helix. (See reference 31.) Instead, they appear to occur in the L1, L2, and L3 loops, in the S2 and S2 domains, and in the β-strands. The suppressor mutations can be used to transfect cells which carry a dominant-negative mutation in p53, or which carry a p53 mutation found in a tumor. They can also be used to transfect cells which contain no p53 due to deletion; or to cells which contain wild-type p53. Cis suppressing mutations can be tested to determine if they function in trans, i.e., when located at a different locus. Cis acting mutations must be tested in the same molecule with a negative mutation This generally requires recombinant techniques to achieve. In contrast, trans acting mutations can be tested on separate molecules. Suitable cells for testing include yeast, bacteria, and mammalian cells.

Nucleic acids encoding p53 containing trans acting suppressor mutations can be used to treat cancer cells so that the neoplastic phenotype of the cancer cells is suppressed or apoptosis is induced. Delivery of p53-encoding DNA molecules to human tumors is known in the art. Any such technique can be used.

According to another aspect of the invention, potential therapeutic agents can be identified. Using a cell according to the present invention which has a selectable reporter gene operably linked to a DNA sequence to which human p53 specifically binds and a fusion gene which expresses a dominant-negative allele of human TPS3, one can perform a drug screening assay. Preferably the allele is one found in human tumors. Test compounds can be contacted with such cells and one can select for the ability of the cells to express the reporter gene. Candidate therapeutic agents are able to induce the cell to display the selectable phenotype of the reporter gene.

Another method for which the strains of the present invention are particularly suited is a screening assay for putative, carcinogens. The Salmonella/mammalian-microsome mutagenicity test developed by Bruce Ames and co-workers has confirmed many carcinogens as mutagens and has identified numerous new mutagens. The test is based on a prokaryotic system with reporter genes which play no role in human carcinogenesis. A eukaryotic system which tests the mutagenicity of compounds on, for example, tumor suppressor genes aids in the classification of and risk assessment for mutagens/carcinogens.

For the tumor suppressor gene p53 there are several examples of mutagens which cause specific mutations in the p53 sequence. Theses include, amongst others, UV light leading to skin cancer and aflatoxin B1 leading to hepatomas. The causal relationships could only be demonstrated because of strong epidemiological data for exposure to a single or few mutagens and a high incidence of the cancer. Similar causal relationships may exist for other mutagens and cancers; however, they are more difficult to prove because there is concomitant exposure to various mutagens and a lower incidence of the specific cancer. A eukaryotic mutagenicity assay for the p53 gene enables the identification of mutagens that cause a specific pattern of p53 mutations.

Using a strain which has a counterselectable reporter gene operably linked to a DNA sequence to which human p53 specifically binds and a fusion gene which expresses human p53 in the cell, one can test putative carcinogens by contacting them with the cell. Using the counterselection, one can identify carcinogens which have induced mutations in TP53. If desired the particular mutations can be identified, for example, by sequencing. Thus particular mutational fingerprints on TP53 of the carcinogens can be identified. Such fingerprints can be used epidemiologically, for example to assess the effects of particular carcinogens on populations.

If desired, one can incubate putative carcinogens with a mammalian liver lysate prior to the incubation with the tester cells. Such liver lysates are able to metabolize pre-carcinogens to carcinogens, as occurs in the human or animal body.

The assay can be performed, for example, using a yeast strain which is homozygous diploid for the reporter gene UAS53::UR43 and which contains a single copy of wild-type p53 on a centromeric plasmid. Known mutagens, such as UV light, aflatoxin B1 and benzo[α]pyrene, or unknown mutagens are applied to the yeast cells. Mutations which cause a non-functional p53 protein lead to a phenotype change from $Ura^+Foa^S$ to $Ura^-Foa^R$ which can be easily screened for. Based on our experience with the system, other mutations can also lead to Foa resistance, most of which are recessive mutations in the UAS53::URA3 reporter gene. By using a strain which is homozygous diploid for the reporter gene the frequency of these mutations will be reduced to $1 \times 10^{-6}$ and should therefore be negligible. In addition, a second wild-type p53 expression construct can be integrated into the genome. Thus the assay will preferentially identify dominant-negative p53 mutations. The plasmids with the mutated p53 genes can be recovered from yeast, expressed in E. coli, purified, and sequenced.

The yeast assay for carcinogenic compounds can be performed in the following way:

1. Homozygous diploid UAS53::URA3 yeast cells which are His⁻ and which bear an episomal p53 expression plasmid with a HIS3 marker gene are plated as a lawn onto -His plates.

2. Crystals, impregnated filter paper disks, or droplets of the compound(s) to be tested are applied to the lawn, setting up a gradient of the compound as the test cells grow. If the test compound has strong mutagenic potential, p53 mutants arise at higher frequencies in the zones containing higher concentrations of the compound.

3. The lawn of cells is transferred by replica-plating, to a -His plate containing 5-Foa, selecting for the p53 plasmid. Only p53 mutants should grow on these plates, Mutagenic effect on ps3 is observed as a halo of Foa-resistant colonies surrounding the spot at which the compounds were originally placed.

4. The plasmids bearing pS3. mutations are recovered from the yeast colonies. The nature of the mutation(s) can-be determined by DNA sequencing.

Note that step 1 can be performed, as in the Ames test, by the inclusion of a rat liver homogenate on the plate, providing the enzymes (mixed function oxygenases, cytochrome P-450s, etc.) that can activate certain pre-carcinogens to carcinogens. Furthermore, yeast strains with mutations in important DNA repair enzymes can be used in order to increase the sensitivity of the test.

Because our system is yeast-based there are two ways in which p53 mutagenesis may be different from mutagenesis in human cells. i) There is no DNA methylation in yeast. Thus mutagens which affect methylated bases will not be active in the assay. This can be overcome (if necessary) by expression of the appropriate methyltransferase(s) in yeast. ii) p53 nucleic acid lacks introns, thus mutations at splice junctions will not be represented. These are known, however, to be very rare events based on the sequence information of p53 mutations in human cancers. Additionally, some compounds may not be able to enter the yeast cells because of their cell walls. This can be circumvented by the preparation and use of spheroplasts or by the utilization of yeast strains with mutations which affect cell permeability.

The strains of the present invention also lend themselves to methods for identification of other cellular components which interact with p53, either stimulating or inhibiting its binding to its specific binding sequences. Using a counterselectable reporter gene and a TPS3 expression construct, one can introduce a library of human nucleic acid molecules each of which is operably linked to expression control sequences. Selecting against the reporter gene using a counterselective agent, e.g., 5-FOA in the case of URA3, identifies individual clones which contain a human nucleic acid which inhibits p53 activity, possibly by means of the protein which the nucleic acid encodes.

This method was tested in a pilot study. A reporter strain (UASS53::URA31p53) was transformed with exon 2 of the SV40 laze T antigen (TAg), a viral antigen known to prevent DNA binding and transactivation by p53. The large T antigen plasmid pGAD-12 was. originally designed for a two-hybrid screen and encodes a Gal4 transactivation domain-TAg fusion. The large T antigen fusion protein was able to interfere with p53 activity in our system, changing the phenotype from Foa$^S$ to Foa$^R$, while the control vector plasmid p GAD-2F encoding the Gal4 transactivation domain alone was unable to do so.

Kits are also contemplated as part of the invention which comprise useful sets of yeast strains and/or plasmids. In one contemplated kit, three strains are provided. A first yeast strain contains a centromeric plasmid. The plasmid contains a gene fusion of a yeast alcohol dehydrogenase promoter operably linked to a human p53 coding sequence; and a yeast histidine (HIS3) gene. The first yeast strain also contains an integrated reporter gene which consists of a p53 consensus binding sequence inserted-upstream from the URA3 locus. This strain can be used for selection of TPS3 mutants. The other two strains can be used for genetic characterization of the TPS3 mutants which are isolated. The second yeast strain contains an integrated reporter gene which consists of a p53 consensus binding sequence inserted upstream from the URA3 locus, within a distance short enough so that binding of p53 activates URA3 transcription. The third yeast strain contains a centromeric plasmid which contains a fusion of a yeast alcohol dehydrogenase promoter operably linked to a human p53 coding sequence, and a yeast LEU2 gene. The third yeast strain also contains an integrated reporter gene which consists of a p53 consensus binding sequence inserted upstream from the URA3 locus. The first strain is of a compatible mating type to the second and third strains, such that the first strain can be mated with each of the others to form diploid cells. Examples of each of these strains are provided in Table 1. Uses of these strains are discussed throughout. Written instructions for performing any of the assays described herein may also be enclosed in the kit, as well as media and selective agents. Strains are typically packaged separately and then bundled or held together in a common container.

Also provided by the present invention is a tripartite gene fusion suitable for integration into the yeast genome. The gene fusion contains a human p53-specific DNA-binding site, a yeast URA3 gene, and a portion of a yeast SPO13 gene. The human p53-specific DNA-binding site is upstream of the URA3 gene, and the portion of the yeast SPO13 gene is interposed between the URA3 gene and the human p53-specific DNA-binding site. The portion of the yeast SPO13 gene consists of the first 15 codons of SPO13 and nucleotides upstream thereof, until nucleotide −170. Importantly, the SPO13 upstream region contains a URS (upstream repressing sequence) that prevents basal low level transcription of URA3. Such a construct is disclosed in detail below, and can be used in formation of strains useful for the practice of the disclosed methods.

The following examples are provided for exemplification purposes only and are not intended to limit the scope of the invention.

EXAMPLES

Example 1

Yeast strains, plasmids and isolation of TP53 mutants.

All of the yeast media used here (e.g. -His) were dropout media based on synthetic complete supplemented minimal medium (14) lacking the indicated nutrient(s). The yeast strains and plasmids used are described in Table 1.

TABLE 1

Yeast strains

| Strain | Relevant genotype* | Plasmids (markers)† |
|---|---|---|
| RBy33 | MATa 1cUAS53::URA3 | — |
| RBy41 | MATa 1cUAS53::URA3 | pRB16 (ADH-p53 HIS3 CEN) |
| RBy159 | MATa 1cUAS53::URA3 | — |
| RBy160 | MATa 1cUAS53::URA3 | pLS76 (ADH-p53 LEU2 CEN) |
| RBy161 | MATa 1cUAS53::URA3 | pLS76 (ADH-p53 LEU2 CEN) pRB17 (ADH-p53 TRP1 CEN) |
| RBy162 | MATa ura3-52 | pLS76 (ADH-p53 LEU2 CEN) |

*All strains listed (except RBy162) are also lys2Δ202 trp1Δ63 his3Δ200 leu2Δ1. RBy162 is also lys2Δ202 trp1Δ63 his3Δ200 leu2Δ1 ade2Δ.
†pRB16 and pRB17 were derived from pLS76 (15) by subcloning the XhoI-SacI fragment containing ADH-p53 (including the CYC1 transcription terminator) into CEN vectors pRS413 and pRS414 (16), respectively.

Construction of Reporter Gene

We fused the SPO13 promoter to a sequence encoding a fusion protein with the first 15 amino acids of SPO13 and the URA3 protein (SPO13::URA3 in pPL128). The SPO13::URA3 fragment was excised from pPL128 and cloned into a pBSK plasmid (Stratagene). The resulting plasmid, pMV252, contains EcoRI sites at −170 and −368 in the SPO13 promoter.

For construction of the UAS53::URA3 reporter genes, oligonucleotides corresponding to the p53 consensus DNA binding site (JB820:5'-AATTTAGGCATGTCTAGGCATGTCTA-3' (SEQ ID NO:2) and JB821-5'-AATTTAGACATGCCTAGACATGCCTA-3' (SEQ ID NO:2) (14) were annealed, phosphorylated, and ligated into EcoRI-digested pMV252.

The UAS53::URA3 alleles were integrated at the ura3-52 locus by homologous. recombination of the product of a PCR reaction. The 5' primer used was JB516 that contains 40 nucleotides of the URA3 sequence upstream of its promoter (−257 to −218) fused to 20 nucleotides of the SPO13 promoter (−370 to −351 (11)):5'-GAAGGTTAATGTGGCTGTGGTIT-CAGGGTCCATAAAGCTITOCCTGGAAGTCTCATGGAG-3'(SEQ ID NO:3). The 3' primer used was 3'URA3 (URA3 -sequence +656 to +632 (12)):5'-TCAGGATCCCRAGGITCCTTGTTACTTCITCCG-3' (SEQ ID NO:4).

Isolation of Independent TP53 Mutations

For isolation of independent TP53 mutations, patches of single colonies from RBy41 (containing an ADH-pS3 HIS3 expression vector (pRB16) and the integrated reporter gene 1cUAS53::URA3) were grown on synthetic complete medium without histidine (SC -His plates), replica-plated to SC -His +0.15% 5-fluoro-orotic acid (Foa) plates and incubated for 2 to 4 days at 37° C. until 5-fluoro-orotic acid resistant ($Foa^R$) papillae emerged.

Only one single $Foa^R$ colony was isolated from each parental patch. These $Foa^R$ clones were 1) mated to RBy159 (MATα, isogenic to RBy41, but lacking an ADH-p53 expression vector) and replica-plated to SC -Ura plates and 2) mated to RBy160 (RBy159 with the ADH-p53 LEU2 plasmid pLS76 (15)) followed by replica-plating to SC -His -Leu plates to select for diploids and then SC -His -Leu +0.15% Foa plates to evaluate the dominance/recessivity of the $Foa^R$ phenotype. Clones which were $Ura^+$ in mating assay #1 and $Foa^S$ in assay #2 were recessive and were not due to TP53 plasmid-dependent mutations. Most of these clones represent recessive mutations that knock out 1cUAS53::URA3. Clones which were $Ura^-$ in assay #1 and $Foa^s$ in assay #2 were TP53 plasmid-dependent recessive mutations. Only clones which were $Foa^R$ in assay #2 potentially contained a dominant-negative TP53 plasmid-dependent mutation; these were further characterized by growing them non-selectively and isolating strains which had lost the (potentially mutated) pRB16. A wild-type TP53 expression plasmid was then introduced into these strains as follows. The plasmid-free strains were mated to RByl62 (MATα ura3-52 and containing pLS76), replica-plated to SC -Ade -Leu plates to select for diploids, followed by replica-plating of the diploids to SC. -Leu +0.15% Foa plates. $Foa^R$ clones which regained their $Foa^S$ phenotype as a result of these manipulations were judged to contain dominant-negative TP53 plasmid-dependent mutations.

Example 2

Identification and classification of dominant-negative TP53 mutants.

We isolated a total of 49 independent spontaneous p53 mutants that behaved in a dominant-negative fashion. These mutants were identified using a two-step selection procedure. In the first step, haploid yeast colonies deficient in URA3 expression were selected on plates containing Foa. In the second step, these colonies were mated to strains containing either the wild-type reporter gene or one copy of wild-type ADH-p53 and subsequently transferred to plates containing Foa. Dominant-negative alleles of TPS3 showed an $Foa^R$ phenotype in both cases. Recessive alleles of TP53 or cis-acting reporter-linked mutations exhibited an $Foa^S$ phenotype in the presence of an additional copy of wild-type ADH-p53 or the wild-type reporter gene, respectively.

Characterization of TP53 mutants. The mutant pRB16 plasmids from all identified dominant-negative TP53 plasmid dependent clones were recovered in bacteria (17), retransformed into RBy33 (RBy41 without pRB16) and the phenotypes rechecked. The dominant-negative phenotypes were then further classified by testing the degree of the dominance over one or two doses of wild-type ADH-pS3 as follows. The retransformed strains bearing mutant pRB16 derivatives were mated to RBy160 and RBy161 1 (RBy159 containing two ADH-p53 expression plasmids, pLS76 (15) and pRB17, which is identical to pRB16 except for the selectable marker TRP1 (16)), replica-plating them to SC -His -Leu and SC -His -Leu -Trp plates respectively, replica-plating them to the same selective plates with 0.15 % Foa and incubating them at 30° C. for 2 to 4 days.

Some of the dominant-negative TP53 mutants were isolated as false positives from a nucleic acid library screen that is irrelevant to this invention; these mutants were characterized in the same fashion (Table 2). Due to the fact that this subset of the mutants studied did not necessarily represent indent isolates; a numerical analysis of mutation frequencies within this subset would be meaningless.

The recessive plasmid-dependent TP53 mutants were also recovered into bacteria and retransformed. .These isolates (as well as the dominant isolates) were evaluated by immunoblotting with anti-p53 antibody PAb 1801, performed as described. RBy50 pRS413 (16) in RBy33) was used as the negative control.

TABLE 2

Properties of independent TP53 mutations selected in yeast

| | |
|---|---|
| Total number of $Foa^R$ clones | 717 |
| Number of TP53 plasmid-dependent mutants | 111* |
| Recessive mutants | 67 (9%) |
| Dominant mutants | 31 (4%)† |
| class 1 | 13 |
| class 2 | 18 |

*13 plasmid-dependent mutants could not be classified, since they did not show consistent phenotypes before and after plasmid recovery and retransformation.
†18 additional independent dominant-negative mutants were obtained as false positives in a cDNA library screen. These mutants are independent by virtue of a unique mutation and are idenfified by * in Table 3.

Recessive mutations in the reporter gene were found in 87% and in the TP53 gene in 9% of all mutants. 4% of the $Foa^R$ colonies contained dominant-negative TP53 mutations (Table 2). Once the dominant-negative TP53 mutants had been identified, the TP53 plasmids were recovered and transformed into a fresh reporter strain (RBy33) to exclude artifacts of the original strain. In all cases the same dominant-negative phenotype could be reproduced. The dominant-negative mutants could be further classified by mating them to a strain with two wild-type ADH-p53 plasmids thus characterizing the dominance of the mutant proteins in the presence of two doses of the wild-type ADH-p53 gene. The most dominant mutants were able to interfere with one and two copies of wild-type ADH-p53 (class 1). Less dominant TPS3 mutants could only override the activity of a single wild-type allele (class 2) (FIG. 1). These classes represented 43% and 57% of the dominant-negative TPS3 mutants, respectively.

Example 3

Sequences of the dominant-negative TP53 mutants.

We then sequenced the core domains (codons 102–292) of the 49 dominant-negative mutants.

Miniprep DNA (17) for the plasmids was RNase treated (7 mg/ml, 10 min. 37° C.), extracted with phenol/chloroform and sequenced with Taq polymerase (Perkin-Elmer) using Prizm kit dye-terminator cycle sequencing on an Applied Biosystems 373A Stretch automated sequencer. Sequences were analyzed using Sequencher software (Gene Codes Corporation, Inc., Ann Arbor, Mich.) for the Macintosh. The core domains of ADH-p53 were sequenced using primers JB990 (5'-ACCAGCAGCTCCTACACC-3' (SEQ ID NO:5)) and JB991 (5'-GAGGAGCTGGTGTTGTTG-3') (SEQ ID NO:6). Eight dominant-negative clones (bold numbers in Table 3) were further analyzed by ligating NcoI/eStuI fragments with the mutations (base pairs 477 to 1039) into pRB16 using standard methods (18). Wild-type sequence for the C-terminal parts of these fragments was verified by sequencing with primers JB1052 (5'-CCATCCTCACCATCATCAC-3' (SEQ ID NO:7)) and JB1091 (5'-GCAGGGGAGGGAGAGATGG3') (SEQ ID NO:8). The hotspot mutations for codons 175 and 249 (in Table 3) were cloned into pRB16 using the same strategy. Phenotypes were checked as described above.

Forty-one of the dominant-negative mutants had a single missense mutation and 8 -had an in-frame deletion. Very strikingly, the mutations clustered around five of the six known hotspot codons in the TP53 gene: 245, 248, 249, 273 and 282 (1, 2, 4). We identified 5 mutations in codon 245, 2 in 248 and 2 in 273. 88% of the missense mutations hit the five hotspot regions for mutations (132–143, 151–159, 172–179, 237–249 and 272–286) or codons for which germline mutations have been described (FIG. 2) (2, 5, 7, 27, 28). 96% of the mutations we recovered in yeast have been described in human cancers or cancer cell lines (Table 3) (4, 29, 30). Our screen hit 5 of the 7 amino acids important in direct DNA binding (codons 241, 248, 273, 277 and 280) and 3 of the 4 amino acids involved in zinc atom contact (codons 176, 179 and 242) (31–33).

With the exception of H179N, all of the most dominant mutations (class 1) localized to codons 241–248 and 277–281. 83% of the mutations in these two regions had the class 1 phenotype (FIG. 2) indicating a strong correlation between the location of mutations and their degree of dominance.

TABLE 3

Sequence data on dominant-negative p53 mutations selected in yeast

| Mutation Number | Codon | Mutation Nucleotide | Amino Acid | Class | described in cancer (29, 30) |
|---|---|---|---|---|---|
| 32* | 127 | TCC->CCC | Ser->Pro | 2 | no |
| 27* | 132 | AAG->AAC | Lys->Asn | 2 | yes |
| 26* | 135 | TGC->TTC | Cys->Phe | 2 | yes |
| 43* | 151 | CCC->CGC | Pro->Arg | 2 | yes |
| 67 | 151 | CCC->CAC | Pro->His | 2 | yes |
| 30* | 158 | CGC->CCC | Arg->Pro | 2 | yes |
| 76 | 176 | TGC->CGC | Cys->Arg | 2 | yes |
| 17* | 179 | CAT->AAT | His->Asn | 1 | yes |
| 50* | 236 | TAC->GAC | Tyr->Asp | 2 | yes |
| 64 | 241 | TCC->TTC | Ser->Phe | 1 | yes |
| 70 | 242 | TGC->TTC | Cys->Phe | 2 | yes |
| 13* | 244 | GGC->GAC | Gly->Asp | 1 | yes |
| 14* | 244 | GGC->AGC | Gly->Ser | 1 | yes |
| 12* | 245 | GGC->AGC | Gly->Ser | 1 | yes |
| 16* | 245 | GGC->CGC | Gly->Arg | 1 | yes |
| 55 | 245 | GGC->AGC | Gly->Ser | 1 | yes |
| 57 | 245 | GGC->AGC | Gly->Ser | 1 | yes |
| 101* | 245 | GGC->GAC | Gly->Asp | 1 | yes |
| 41* | 246 | ATG->ATT | Met->Ile | 2 | yes |
| 62 | 246 | ATG->AGG | Met->Arg | 1 | yes |
| 1* | 248 | CGG->TGG | Arg->Trp | 1 | yes |
| 63 | 248 | CGG->TGG | Arg->Trp | 1 | yes |
| 48* | 252 | CTC->ATC | Leu->Ile | 2 | no |

TABLE 3-continued

Sequence data on dominant-negative p53 mutations selected in yeast

| Mutation Number | Codon | Mutation Nucleotide | Amino Acid | Class | described in cancer (29, 30) |
|---|---|---|---|---|---|
| 65 | 252 | CTC->ATC | Leu->Ile | 2 | no |
| 20* | 257 | CTG->CCG | Leu->Pro | 2 | yes |
| 37* | 257 | CTG->CAG | Leu->Gln | 2 | yes |
| 36* | 259 | GAC->TAC | Asp->Tyr | 2 | yes |
| 29* | 265 | CTG->CCG | Leu->Pro | 2 | yes |
| 69 | 273 | CGT->CCT | Arg->Pro | 2 | yes |
| 74 | 273 | CGT->CCT | Arg->Pro | 2 | yes |
| 7* | 277 | TGT->TAT | Cys->Tyr | 1 | yes |
| 28* | 278 | CCT->CAT | Pro->His | 2 | yes |
| 38* | 278 | CCT->TCT | Pro->Ser | 2 | yes |
| 10* | 279 | GGG->GAG | Gly->Glu | 1 | yes |
| 53 | 279 | GGG->GAG | Gly->Glu | 1 | yes |
| 61 | 279 | GGG->GAG | Gly->Glu | 1 | yes |
| 8* | 280 | AGA->ACA | Arg->Thr | 1 | yes |
| 58 | 280 | AGA->AGC | Arg->Ser | 1 | no |
| 3* | 281 | GAC->GGC | Asp->Gly | 1 | yes |
| 5* | 281 | GAC->TAC | Asp->Tyr | 1 | yes |
| 56 | 281 | GAC->GGC | Asp->Gly | 1 | yes |
| 18*, 68, 71, 72, 73, 75 | Δ175–180 (or 176–181 or 177–182†) | | | 2 | yes |
| 35* | Δ216 (or 217 or 218)‡ | | | 2 | yes |
| 42* | Δ252–254 (or 251–253)§ | | | | |
| 175¶ | | CGC->CAC | Arg->His | 2 | yes |
| 249¶ | | AGG->AGT | Arg->Ser | 1 | yes |

Bold clones were characterized further by cloning the mutation into wild-type ADH-p53 and rechecking the phenotypes.
*These dominant-negative mutations were obtained as false positives in a cDNA library screen.
†This deletion presumably arises frequently because of the direct repeat GCGCTGC present at codons 175–176 and 181–182.
‡deletion of one of three tandem GTG codons.
§Direct repeat of ATC flanks deleted nucleotides.
¶These hot spot mutations were cloned into wild-type ADH-p53 since our screen did not identify mutations of these codons.

To exclude that second mutations up- or downstream of the core domain contributed to the described phenotypes, we subcloned NcoI/StuI fragments (codons 159–347 encoding only the mutation of interest as confirmed by sequencing) into a wild-type ADH-p53 plasmid for the following mutants: C176R, D175–180, D217, G2,45D, R248R273P, P278S and D281Y. In all cases the same dominant-negative phenotype was reproduced (FIG. 1, Table 3).

Our screen hit 3 hotspot amino acids (codons 245,.24$ and 273) but failed to identify mutations in the other 3 (codons 175, 249 and 282). These hotspots in human cancers are due in large part to methylation of the CpG dinucleotides present in codons 175 and 282 and exposure to aflatoxin B, for codon 249 (1–4, 8); neither situation applies to our yeast system. Two amino acid substitutions for these- hotspots, R175H and R249S, were subcloned into wild-type ADH-pS3 and shown to prevent UAS53:URA3 transcription. These mutants were also found to be dominant over wild-type (FIG. 1, Table 3).

Example 4

Protein expression levels of dominant-negative TP53 mutants.

The wild-type and the mutant ADH-p53 genes are expressed from the same promoter in our system. In order to investigate whether the dominant-negative phenotypes were partially caused by an increased stability of the mutant protein we analyzed protein levels by immunoblotting with anti-p53 antibody PAb 1801 (34). FIG. 3 shows that protein levels for the mutant p53 proteins were similar to that of wild-type.

Example 5

Analysis of recessive TP53 mutants.

We also analyzed the more abundant recessive TP53 mutants. Since we considered the likelihood of non-missense mutations high, we immunoblotted protein extracts from the 67 independently obtained recessive TP53 mutants. None of these clones showed full-length protein. Four mutants expressed shorter proteins consistent with C-terminal truncation since PAb 1801 recognizes the N-terminus (34).

Conclusions

We have used the methods and strains described here to isolate and analyze TP53 mutations. Based on our work in yeast, where recessive TP53 mutations outnumbered dominant ones by about two to one, we believe that recessive TP53 mutations probably occur at a higher rate in human cells than dominant mutations, but that the recessive mutations are much less likely to lead to cancer (and therefore to be sequenced) since the remaining wild-type allele continues to exert its important functions. Our selection in yeast for dominant-negative TP53 mutations has identified a variety of missense mutations and in-frame deletions whose locations show a striking correlation with the hotspot regions of human cancer mutations. This suggests that the high frequency of human cancer mutations in these hotspot regions is in large part due to their dominant-negative effect on the wild-type p53 protein. Our data shows that the dominant negative mutants interfere with the wild-type protein to varying degrees, thus the amount of residual p53 activity in cells heterozygous for different TP53 mutations is likely to be different. However, even for the strongest dominant-negative mutants, there is likely to be some residual p53 function. The dominant-negative interference with the function of wild-type p53 should lead to elevated rates of DNA damage, chromosome loss, and other forms of loss of heterozygosity of the TP53 locus. Loss of heterozygosity would eliminate the residual activity provided by the wild-type TP53 allele and provide the (pre-)malignant clone with further growth advantages.

Class 1 p53 mutants in our assay are more proficient than class 2 mutants in interfering with wild-type p53 function. The locations of all class 1 mutations correspond closely to areas of the core domain which are essential for the structure of the DNA binding surface of p53 (L2 loop, codons 163–195 and L3 loop, codons 236–251), for major groove contacts in the pentamer sequence of the consensus DNA binding site (H2 a helix of the loop-sheet-helix motif, codons 278–286) and for minor groove contacts in the AT-rich region of the binding site (L3 loop) (31–33). These mutations may be more efficient in destabilizing a heterotetramer of mutant and wild-type p53. Assuming i) a single mutant subunit can poison a p53 tetramer, ii) equal size pools of mutant and wild-type protein and iii) unbiased mixing of mutant and wild-type subunits, heterozygous dominant mutations should lower p53 activity 16-fold. Thus, overexpression of a dominant-negative mutant relative to wild-type is theoretically not required for abrogation of wild-type p53 function, and our experiments in yeast confirm this. These data suggest that the mutant p53 overexpression observed in human cancers represents an additional level of complexity in p53 deregulation.

Example 6

Identification of suppressor mutations

The goal of wild-type p53 activity can theoretically be achieved in two ways: One could confer wild-type activity to the still present p53 mutant (containing either a missense mutation or an in-fame deletion) (45–48). This approach relies-on the identification of small molecules able to stabilize the mutant protein enough to let it perform wild-type p53 functions. These small molecules can be identified by high through-put drug screens in functional p53 assays. In a more rational strategy, one could identify second-site missense mutations capable of suppressing a wide variety of p53 mutations (i.e. the subclass of structural mutants). Structural analysis of these mutants could then be used to design small molecules able to stabilize p53 mutants in a similar fashion.

One could also override the dominant-negative effect of p53 mutants (missense or in-frame deletion) through very high levels of wild-type protein (44–47). Many cancers however already show significant overexpression of the mutant p53 protein, so that wild-type p53 levels able to override the dominant-negative mutant protein may turn out to be unachievable. This problem could be overcome by a "super" p53 molecule which only requires near-normal p53 protein levels in order to restore wild-type ps3 activity.

In pursuit of these objectives we took a genetic approach in yeast in order to first identify missense mutations able to suppress common p53 cancer mutations in cis and to then ask whether such missense mutations, when cloned into wild-type p53 could also suppress cancer p53 mutants in trans. We used our previously described p53 yeast dissociator assay (38, 49, 50) to identify several intragenic missense suppressor mutations for the p53 mutants V143A, G245S and R249S. In addition, we have established that several of these intragenic suppressor mutations (1T23P) N239Y, S240N, and T123A, also function in trans. Thus, these suppressor mutants have the characteristics of proposed "super" p53.

Methods

1. Identification of suppressor mutations in cis

For the identification of suppressor mutations in -cis the following plasmids were used which were identical to pRB16 (ADH-pS3 expression cassette in a HIS31CEN plasmid, (38,50)) except for the indicated missense mutations: pRB212 (R175H), pRB217 (G245D), pRB28 (G245S), pRB218 (R248W), pRB214 (R249S) and pRB219 (R273P). For pBR255 (V143A) the P I fragment of pC53-SCX3 (6,58) was cloned into pRB16. Successful cloning was checked by restriction digestion with Bsg I (recognizing the wild-type codon) and sequencing with primer-JB990 (38).

Our initial strategy was PCR mediated mutagenesis of the entire core domain and gap repair. All of the above plasmids except pRB255 (V143A) were gapped with PflM I. Conventional PCR conditions using Taq polymerase and primers JB1151 (5'-GAGGAGCCGCAGTCAGAT-3'(SEQ IQ NO:9)) and JB11152 (5'-TTTATGGCGGGAGGTAGA-3' (SEQ ID NO:10)) were used to obtain PCR products for the same intact mutant plaids which extended from base pair 4 to 1143 of the p53 ORF (+1 corresponds to the A of the start codon) which overlapped with both ends of the gapped plasmids (FIG. 4).

Taking advantage of S. cerevisiae's high efficiency homologous recombination, the PCR product and the gapped plasmid were cotransformed into RBy33 (containing one integrated copy of 1cUAS::URA3, the p53 dependent reporter gene, (38,50)) (FIG. 5). In general, 0.8 to 3.5 µg of PCR product and 0.2 to 0.85 µg of gapped plasmid were used and gave rise to 0.5 to $8.5 \times 10^5$ His$^+$ colonies. Except for the controls, all transformants were plated onto SC -Ura plates, replica-plated first to SC -His after 2 days, then again to SC -Ura. Ura⁺ colonies were grown nonselectively and replica-plated to SC +Foa 0.1%. Clones that became Foa^R were classified as having considered to have a plasmid dependent Ura⁺ phenotype. A subset of these clones for R175H, G245D and G245S (47/191, 51/130, 57/222, respectively) and all clones for R248W (46), R249S (21) and R273P (2) were then single-colony purified on SC-His-Ura plates. These were grown non-selectively on YPD plates, streaked for single colonies on YPD plates and replica-plated to SC -His and SC -Ura plates to confirm plasmid dependency of the Ura⁺ phenotype by cosegregation of the Ura⁺ and His⁺ phenotypes. These plasmids were rescued (51) and transformed into RBy33 to recheck the phenotypes. 20, 25, 22, 20, 15 and 2 plasmids for R175H, G245D, G245S, R248W, R249S and R273P were sequenced with oligos JB990 an/or JB991 (38) to check whether the original mutation persisted as expected for a suppressor mutation. All of these plasmids showed reversion to the wild-type amino acid except 6. R175H-derived plasmids and 3 G245S-derived plasmids. For one plasmid each of R175L, (pRB235), R175Q (pRB289) and N239Y-(pRB237) an-Nco I/Stu I fragment with the mutation was cloned into pR316 (resulting in pRB303, pRB304 and pRB30i, respectively). Successful cloning (and otherwise wild-type sequence for the fragment) was determined by sequencing with 331052 (38), J!31152, JB1275 (5'-GTTGATTCCACACCCCCG-3') (SEQ ID NO:11) and in addition JB1348 (5'-CAGTGCTCGCTTAGTGCTCC-3' (SEQ ID NO:12)) for R175LQ. Four independent transformants of these plasmids into RBy33 were patched onto SC -His, replica-plated to SC, -URa and SC -His +Foa 0.1% and pictures taken after 2 days. Controls were RBy234 (pRB212 with R175H in RBy33), .RBy198 (pRB28. with G245S in RBy33), RBy41 (RBy33 with pRB16), RByS5 (RBy33 with pRS413 (52)) and RByS7 (BY385 with pRB16 (50)) (FIG. 6A).

Since this strategy primarily yielded true introcodon revertants, we developed a new strategy which selectively mutagenized regions of the p53 ORF adjacent to the staring mutations, but not including them. For V143A we mutagenized the region downstream of codon 143 by gapping the plasmid with restriction enzymes Nco I and Stu I (FIG. 4). Conventional PCR conditions using Taq polymerase and primers JB1275 and JB1276 (5'-AGACCCAAAACCCAAAAT-3' (SEQ ID NO:13)) were used to obtain a PCR product extending from base pair 439 of the p53 ORF to base pair 78 after the stop codon which overlapped with both ends of the gapped plasmid. 0.6 μg of PCR product and 1.2 μg of gapped plasmid were cotransformed (resulting in 3.8×10⁵ His⁺ colonies) and, except for the controls, directly plated onto SC -His -Ura plates and incubated at 30° C., thus selecting for repaired, functional plasmids (His⁺) and possibly a functional p53 molecule (Ura⁺). His⁺Ura⁺ clones were single colony purified, their phenotypes rechecked and further analyzed as above. We studied a subset of 720 Ura⁺ colonies of which 580 were plasmid dependent. 44 clones were sequenced with JB1274 (5'-GCCCATGCAGGAACTGTT-3' (SEQ ID NO:14)) and 42 of them were wild-type. The p53ORFs of the other two plasmids (pRB306 and 307) were sequenced in their entirety using J11990, JB1052 (38), JB31152, JB1275 and JB1348 in order to identify the second-site suppressor mutation. A small Bsu36 I/Stu I fragment of pRB306 with the suppressor mutation N268D was subcloned into pRB255. Successful cloning was verified by sequencing with 1B1348. The phenotypes were reconfirmed for 4 independent transformants of each subcloned mutant in RBy33 as described above. The control strains were RBy41, RByS7, RBy287 (pRB255 with V143A in RBy33) and RBy198.

A similar gap repair strategy was used for the upstream region of G245D, G245S, R248W and R249S. The plasmids were gapped using restriction enzymes BspM I and Bsu36 I (FIG. 4). The overlapping PCR products were prepared using primers JB1273 (5'-CATTTCCATCTATTGAA-3' (SEQ ID NO:15)) and JB1274. 1.2 μg PCR product and 0.6 μg gapped plasmid were cotransformed leading on average to 8.0×10⁵ His⁺ colonies. 68, 308, 26 and 221 His⁺Ura⁺ colonies were isolated of which 12, 93, 4 and 7 were plasmid-dependent, respectively. The presence of the original mutation was checked by sequencing with JB1348 and/or JB991. All 12 plasmids for. G245D and all 4 for R248W showed reversion to the wild-type amino acid. This was also the case for 81 of 88 G245S and 6 of 7 R249S plasmids. 7 plasmids for G245S and 1 for R249S were sequenced entirely using JB990, JB1052, 3B1084 (5'-TTGTTGAGGGCAGGGGAGT-3' (SEQ ID NO:16)), JB1274 and JB1275. For R249S, the double suppressor mutations T123A and H168R (pRB280) were cloned together (using the unique SgrA I/Bsu36 I sites) and separately (using the following sites: BspM I for T123A, Nco I/Bsu36 I for H168R) into pRB214 (resulting in pRB298, pRB294 and pRB296, respectively) (able 4). Successful subcloning was confirmed by digestion with BstX I (recognizing the T123A mutation) for T123A and T123A+H168R and sequencing with JB1274,3131348 and/or JB990 for all 3 subcloning steps. For G245S, the suppressor mutation T123P (pRB284) was subcloned as described for T123A (resulting in pRB290) and sequenced with JB1084, JB1274 and JB1348. N239Y and S240N could not be separated from the original mutation G245S by restriction digestion. Therefore, a Bsu36 I/Stu I fragment containing both G245S and N239Y or S240N was cloned into pRB16 (resulting in pRB301 and pRB308, respectively) (Table 4). These cloning steps were confirmed by digest with Bbv I (recognizing G245S) and sequencing with JB1275 and JB1348. The phenotypes of the plasmids were determined for 4 transformants into RBy33 as described above (FIG. 6B). The controls for all suppressor mutations of G245S were identical to the one for V143A, the controls for the R249S suppressor mutations were RBy41, RByS5 (RBy33 with pRS413) (52), RBy57 and RBy235 (pRB214 with R249S in RBy33) (38, 50).

TABLE 4

Independent intra-codon reversions and second-site suppressor mutations

| | | | | | Confirmatory subcloning | | | Subcloning of suppressor mutations into wt-p53 | | | | |
|---|---|---|---|---|---|---|---|---|---|---|---|---|
| Original mutation | Suppressor amino acid change(s) | Suppressor nucleotide change(s) | Original suppressor plasmid | Original suppressor strain | Cis yeast plasmid | Cis yeast strain | Mammalian plasmid | Cis yeast plasmid | Cis yeast strain | Trans yeast plasmid | Trans yeast strain | Mammalian plasmid |
| R175H | R175L | CGC->CTC | pRB235 | pRBy278 | pRB303 | RBy281 | — | — | — | — | — | — |
| R175H | R175Q | CGC->CAG | pRB289 | pRBy279 | pRB304 | RBy282 | — | — | — | — | — | — |
| G245S | N239Y | AAC->TAC | pRB237 | pRBy280 | pRB305 | RBy283 | — | — | — | — | — | — |

TABLE 4-continued

Independent intra-codon reversions and second-site suppressor mutations

| | | | | | Confirmatory subcloning | | | Subcloning of suppressor mutations into wt-p53 | | | | |
|---|---|---|---|---|---|---|---|---|---|---|---|---|
| Original mutation | Suppressor amino acid change(s) | Suppressor nucleotide change(s) | Original suppressor plasmid | Original suppressor strain | Cis yeast plasmid | Cis yeast strain | Mammalian plasmid | Cis yeast plasmid | Cis yeast strain | Trans yeast plasmid | Trans yeast strain | Mammalian plasmid |
| V143A | N268D | AAC->GAC | pRB306 | pRBy284 | pRB334 | RBy290 | pRB340 | pRB333 | RBy291 | pRB336 | RBy292 | pRB341 |
| V143A | N268D (+A161A) | AAC->GAC (+GCC->GCT) | pRB307 | pRBy285 | — | — | — | — | — | — | — | — |
| G245S | T123P | ACT->CCT | pRB284 | RBy256 | pRB290 | RBy262 | pRB320 | pRB291 | RBy263 | pRB302 | RBy274 | pRB321 |
| G245S | T123P (+M40I) | ACT->CCT (+ATG->ATA) | pRB285 | pRBy257 | — | — | — | — | — | — | — | — |
| G245S | N239Y | AAC->TAC | pRB282 | RBy255 | pRB301 | RBy273 | pRB325 | pRB309 | RBy288 | pRB337 | RBy293 | pRB327 |
| G245S | S240N | AGT->AAT | pRB286 | RBy260 | pRB308 | RBy286 | pRB326 | pRB335 | RBy289 | pRB338 | RBy294 | pRB342 |
| R249S | T123A + H168R | ACT->GCTCA C->CGC | pRB280 | RBy253 | pRB298 | RBy270 | pRB323 | pRB299 | RBy271 | pRB310 | RBy275 | pRB324 |
| | T123A | ACT->GCT | — | — | pRB294 | RBy266 | — | pRB295 | RBy267 | pRB339 | RBy295 | pRB322 |
| | H168R | CAC->CGC | — | — | pRB296 | RBy268 | — | pRB297 | RBy269 | — | — | — |

2. Evaluation of suppressor missense mutations in the absence of the original mutation Mutations T123A, T123P, H168R, T123A+H168R and N268D were subcloned into pRB16 (wild-type p53) as described above (pRB295, pRB291, pRB297, pRB299 and pRB333, respectively) (Table 4)., For N239Y and S240N site-directed mutagenesis was currently performed using the "fusion PCR" approach (53). In brief, using Pfu polymerase and an outer and inner primer each, two PCR products were made in which both inner primers encode the desired mutation. The final PCR product was obtained by using the two outer primers and the two purified PCR products as template. For N239Y, the first set consisted of outer primer JB1151 and inner primer JB1515(5'-CATGCAGGAACTGTAACACATGTAGTTGTAGTGGAT-3' (SEQ ID NO:17)) and the second set of outer primer JB152 and inner primer JB1515 (5'-CACTACAACTACATGTGTTACAGTTCCTGCATGGGC-3' (SEQ ID NO:18)). For S240N, the outer primers were the same, the inner primers were JB1551 (5'-GCCGCCCATGCAGGAATTGTTACACATGTAGTTGTAG-3' (SEQ ID NO:19)) and 3B1550 (5'-CAACTACATGTGTAACAATTCCTGCATGGGCGGCATG-3' (SEQ ID NO:20)), respectively. Stu I/Bsu36 I fragments of the final PCR products were cloned into pRB16. Successful cloning was screened with AlwN for S240N (recognizing the wild-type codon). For both cloning steps the subcloned PCR fragments were sequenced in heir entirety using JB1052, JB1152, JB1275, and JB1348 to exclude the possibility of new mutations introduced by PCR. The phenotype of each p53 mutation was determined for 4 independent transformants in RBy33 as described above (FIG. 7). Controls were identical to the ones used in FIG. 6B.

3. Evaluation of suppressor missense mutations in trans

The XhoI/SacI ADH1/CYC1 expression cassettes (15) bearing mutations T123P, T123A, N239Y, S240N, N268D, and T123A+H168R were cloned into pRS415 (52) and the resulting plasmids (pRB302, pRB339, pRB337, pRB338, pRB336, and pRB310, respectively) transformed into RByl59 (38) (Table 4). The resulting strains (RBy274 and RBy275 respectively), as well as RByl60 (wild-type p53, (38)) were then mated with stains expressing 39 different dominant-negative p53 mutants obtained from (38) and with RBy287 (V143A) and analyzed as described in (38). The controls on all plates were the results of the following matings: RBy57 with RByl62; RByl60 with RBy41 and RBy277 with Rby55 (FIG. 8).

4. Analysis of p53 protein levels

Protein levels were analyzed as described in (50) (FIG. 9).

Results

1. Identification of intra-codon mutations for R175 and intragenic second-site suppressor mutations for V143A, G245S and R249S Our initial strategy consisted of a PCR mutagenesis and gap repair approach in which contained the original mutation was contained within the PCR product. This led to a very high background of reversions of the original mutation to the wild-type amino acid. We used standard PCR conditions and Taq polymerase as opposed to intentionally mutagenic conditions in order to minimize the likelihood of generating multiple missense mutations whose individual roles could only be established by subsequent subcloning and site-directed mutagenesis. We identified 2 amino acids which can substitute for Arginine at codon 175 without losing wild-type p53 activity as measured in our URA3 assay: R175L (5 of 20 sequenced) and R175Q (1 of 20 sequenced). Surprisingly, R175L has been described as a cancer mutation (30, 54). This may indicate that not all missense mutations registered in the cancer database are essential steps toward tumorigenesis. Alternatively, our assay may not appropriately reflect that R175L is deficient in upregulating certain downstream genes or in interacting with proteins important for G1 arrest and/or apoptosis. We also isolated the second-site suppressor mutation N239Y for G245S (3 of 22 sequenced) which we again obtained with our second approach. For these experiments, we did not sequence all plasmids in their entirety and thus did not establish how many isolates were independent (Table 4).

In the second selection scheme we utilized the same general strategy. In an effort to reduce reversions to wild-type p53 we excluded the original mutation from the PCR product. This design was clearly superior, even though a significant background of reversions to wild-type remained. In this initial study we concentrated on the regions upstream of G245D, G245S, R248W and 249S and the region downstream of V143A, mostly for convenience reasons (FIG. 4). Our experiments for G245D (12 plasmids analyze and R248W (4 plasmids analyzed) yielded no suppressor mutations which may be due to several reasons: 1) our screen was not exhaustive enough, 2) there are very few or no suppressor mutations for these two p53 mutants or 3) we mutagenized an uninteresting portion of the p53 coding region. The last reason derives some validation from a recent study by (55) which described a suppressor mutation T284R obtained on the basis of modeling studies. This mutation was able to suppress p53 mutants R248W R273C and R273H, even though depending on the assay it required additional artificial activation of R248W and R273C via C-terminal truncation. For V143A, G245S and R249S 44, 88 and 7 plasmids were analyzed of which 2, 7 and 1 showed persistence of the original mutations. The following single amino acid substitutions were identified as cis suppressors: for V143A the suppressor mutation N268D (2 independent clones) and for G245S mutations T123P (4 total, 2 independent), N239Y (2 total) and S240N (1 total) Cable 4). For R249S, a single isolate with 2 missense mutations, T123A and H168R was identified (Table 4). By sequencing and subcloning of fragments with the suppressor mutations we confirmed that these mutations alone were sufficient to suppress the original mutation FIG. 7)). Within the detection levels of our assay, all suppressor mutations except T123P and S240N (phenotype $U^+F^R$ instead of $U^+F^S$) led to complete restoration of wild-type p53 activity. Both the T123A and H168R mutations were required to suppress R249S. Neither alone showed partial suppression of R249S (FIG. 6B).

It is interesting to examine whether any of the newly characterized second-site suppressor mutations in codons 123, 168, 239, 240, or 268 have been observed in human cancers. If these mutations improve or do not abrogate the function of p53, they are expected to be under-represented in or absent from human tumors. Comparison with the database for cancer mutations (30,54) showed that no missense mutations have been reported for codons 118 to 124. For codons 239, 240 and 268 missense mutations have been found, but not those amino acid substitutions identified by us. The only mutation isolated by us as a suppressor and reported in cancer is H168R (see FIG. 10 for the locations of mutant residues in the core domain). Consistent with this data, all suppressor mutations cloned into wild-type p53, including T123A+H168R have the wild-type phenotype $U^+F^S$(FIG. 7). However, H168R by itself has the phenotype $U^+F^R$ indicating a partial loss of wild-type function (FIG. 7).

2. Evaluation of suppressor mutations combined-with other p53 mutations

Our goal was the identification of mutations whose mechanism of suppression can be applied to other p53 mutants. Based on the crystal structure of the pS3 core domain with a p53 consensus DNA binding site (31–33, 37) we propose the following interpretation of their mechanisms: N239Y and S240N probably make new DNA contacts. In the crystal structure, T123 is close to, but not directly at the interface between DNA and the p53 core domain. We think that the two T123 mutations may stabilize the DNA binding surface of the core domain, H168R appears to compensate directly for R249S (FIG. 10, 11). This fits with the observation that H168R by itself interferes with p53 activity in cis in our assay. The first two mechanisms (new DNA contacts and stabilization of the DNA binding surface) may represent more universal forms of suppression and hence could in principle reverse the effects of other p53 mutations. Further subcloning will be required to test how universally these mutations suppress.

N268D may be the most interesting candidate for a general suppression mechanism which could be exploited for rational drug design. N268D clearly does not compensate directly for V143A, but is predicted to make a new hydrogen bond with the backbone amide of codon 111 (or less likely codons 110 or 102). This may represent a general mechanism for stabilization of the hydrophobic core of p53; thus this mutation might suppress a broad range of structural and even DNA contact mutants. For that reason we are currently subcloning N268D into several structural and DNA contact mutants.

3. Evaluation of suppressor missense mutations in trans

Our p53 yeast dissociator assay allows us to rapidly evaluate the suppressor mutations for their activity in trans. We have analyzed all identified suppressor mutations and in addition T123A alone using a dominance assay we have previously described (38). In this assay, we evaluated whether these versions of p53 bearing the suppressor mutations in otherwise wild-type5ps3 were recessive like wild-type p53 or whether they were immune to the effects of dominant-negative p53 mutants. If the latter was true, these mutant forms could be considered "super" p53 molecules able to function in the presence of dominant-negative and carcinogenic forms of p53. Reporter strains with HJS3ICEN p53 expression plasmids bearing missense mutations (36 total) and, in-frame deletions (3 total) were mated to strains with LEU21CEN plasmids expressing either of the suppressor constructs or wild-type p53. As previously shown, all dominant-negative p53 mutants could override wild-type pS3 and thus lead to Foa resistance in the diploid (FIG. 8). The same was true for the T123A+H168R and N268D forms of p53 which were recessive to the p53 mutants as well (FIG. 8). This included recessivity to the cancer mutations which these suppressor mutations had suppressed in cis (FIG. 6B). However, T123P was immune to the entire collection of dominant-negative mutations (39/39). This effect could be seen after two days of incubation (FIG. 8) and persisted even after five days (data not shown). T123A, N239Y and S240N could suppress the mutant phenotype as well, but not to the extent of T123P. All of them showed some Foa resistance in the presence of cancer mutants. After 5 days of incubation it appeared that N239Y and S240N were slightly stronger suppressor mutations than T123A.

4. Protein levels for wild-type p53 and several suppressor constructs

One explanation for the strong suppressor activity in trans of T123P could be elevated protein levels, which would increase the likelihood of functional T123P homo-tetramers and thus UR43 expression. To evaluate this possibility we compared strains with one and two plasmids encoding wild-type p53 to stains with one plasmid encoding the suppressor constructs T123P and T123A+H168R. The suppressor mutants showed equal or slightly decreased protein levels as compared to wild-type p53, definitively ruling out this interpretation FIG. 9). We are currently performing the same studies for other suppressor mutations. We also are starting to look at the possibility that T123P and the other suppressor mutations which function in trans have an increased affinity for p53 DNA binding sites, thus overriding mutant p53 subunits even in a heterotetramer.

5. Evaluation of suppressor mutations in cis and trans in mammalian assays

It is important to demonstrate the above described features of the suppressor mutants in mammalian cells. We use transient transfection assays in SAOS2 cells which are null for p53 to show their ability to transactivate the p53 dependent reporter gene luciferase, induce G1 arrest and suppress colony formation. We also determine by immunoblotting their ability to activate several downstream genes important for induction of G1 mW and Spots. These assays address the question of their activity in trans by cotransfecting various ratios of mutant and suppressor or wild-type plasmids.

Discussion

We have identified several mutations that suppress in cis the effects of common p53 cancer mutations. Some of these mutations, i.e. H168R appear to have a mode of action which is very allele-specific. Others (T123A, T123P, N239Y and S240N) may turn out to suppress at least a subset of p53 mutants in cis. Based on our current knowledge these suppressors may be of somewhat limited value for a rational drug design approach for different reasons: if N239Y and S240N do make new DNA contacts, this may be difficult to recreate with small molecules. The mechanisms of suppression for T123A and T123P are at hiss point not obvious based on the available structural data which makes it difficult to predict their usefulness for drug design. Structural studies on the mutant proteins and protein/DNA complexes will be required to resolve these questions.

The suppressor mutation N268D (for V143A) appears to be the most promising candidate in terms of designer drugs. This is based on the prediction that N268D is capable of stabilizing the β-sandwich of the p53 core domain by establishing a new hydrogen bond with (most likely) codon 1 1. VI 43A is a well-studied member of a large and diverse class of hydrophobic core mutations. A universal suppressor for this class of mutants could guide the design of a very useful p53-core stabilizing drug. We are in the progress of testing this hypothesis by subcloning N268D into several structural mutants as well as into representative DNA contact mutants. Should N268D turn out to be a general suppressor for at least the structural mutants, it will be especially worthwhile to study the crystal structure of this suppressor mutant.

Our p53 yeast dissociator assay allows us to rapidly analyze the ability of the suppressor mutations to act in Us. To our own surprise, T123P, a mutation which only partially suppresses G245S in cis, appears to be a universal suppressor of p53 mutants in trans. It will be helpful to quantitate the suppressive effect of T123P in yeast using other reporter genes (i.e. lacZ) with different p53 binding sites. T123A, N239Y, and S240N also are suppressor mutations which function in trans. However, their suppressive effect does not match those of T123P. N268D and the combination of T123A +H168R showed no suppressor activity in trans. (FIG. 8)

For T123P, we have ruled out the most trivial explanation for this super-dominant phenotype by anti-p53 immunoblotting: it is not caused by increased levels of the suppressor protein. This result makes it very likely that T123P has a highly increased affinity for p53 binding sites, to the extent that it can override the dominant-negative effects of p53 mutants in a hetero-tetramer. We are currently addressing this question. In addition, it cannot be excluded that T123P has unique structural properties (with a DNA binding affinity similar to wild-type p53) that allow it to stabilize an otherwise non-functional hetero-tetramer. Studying of the crystal structure of this suppressor mutant will provide further invaluable insight into its mechanism. It will also be very important to determine the protein levels and DNA binding affinities of the remaining suppressor mutations. If increased binding affinity plays an important role, combinations of T123P with either N239Y or S240N may produce an even more efficient "super" p53. In this context it is interesting to note that T123A by itself in trans, since it was found to have a five-fold increased DNA binding affinity in a previous independent study (56).

To our knowledge, this is the first report of suppressor mutants which can override the dominant-negative effect of a wide variety of p53 mutants at equal protein concentrations. This finding is of significant importance in view of the continuing efforts to develop gene therapy with p53 as a viable therapeutic modality (44, 45, 46, 47). Gene therapy with wild-type p53 is confronted, besides questions of the most efficient delivery vehicle, with the fact that a large number of dominant-negative p53 mutants is present at markedly increased intracellular levels (1, 36, 44). Therefore, it may be impossible to achieve the levels of wild-type p53 able to override the dominant-negative effect and thereby efficiently induce apoptosis in the cancer cells. This problem may be solved by using "super" p53 molecules, such as T123P, which only need to be present in equal, or potentially lesser amounts than the mutant protein. Toward these goals it will be important exactly to delineate the activation of downstream genes for this suppressor mutant and its behavior in various cell types. It is conceivable that suppressor mutants like T123P, N239Y, and S240N actually lead to a different cellular response which could be of significant therapeutic advantage, Le., apoptosis in cancers derived from epithelial cells instead of the more likely G1 arrest. It is also of interest lo identify further suppressor mutations which can act in trans. Combinations of such mutations may turn out to be a more powerful tool.

The dominant-negative effect of p53 mutants can theoretically also be circumvented by design of a hybrid protein of mild-type p53 with a heterologous oligomerization domain as described by (57). However, since these hybrid proteins should be able to force other cellular proteins (most likely completely unrelated to p53 biology) into heterotetramers, the biological effects of these hybrid proteins would have to be studied very carefully prior to any studies in human beings.

The current study has by no means been exhaustive. Further screens for suppressor mutations of other common p53 mutants will provide additional insights and may lead to more efficient combination suppressor mutants and different targets for drug design. This genetic approach in yeast using a functional assay for p53 has proven to be very powerful and will undoubtedly lead to a better understanding of p53 mutants. Based on our experience, these screens can be improved in two ways. We had a surprisingly high background of reversion to wild-type in the original mutations despite exclusion of these codons from the PCR product. This problem can be addressed by using codons for the mutant amino acid which are very unlikely to revert back to wild-type (i.e. TCG for Serine requires two base pair changes for reversion to the wild-type codon Arginine). One could also analyze the up- or downstream regions of in-frame deletions. Thus far, we have intentionally limited ourselves to standard PCR conditions, thus biasing our results to those amino acid changes which can be achieved by single base pair changes. A broader spectrum of suppressor mutations could be obtained by using "mutagenic" PCR conditions. One could also directly search for suppressor mutations acting in trans by mutagenising a wild-type p53 expression plasmid and testing the resulting plasmids in the described mating assays for their dominance over p53 cancer mutants.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES CITED

1. Hollstein, M., Sidransky, D., Vogelstein, B. & Harris, C. C. (1991) *Science* 253, 49–53.
2. Caron de Fromentel, C. & Sopssi, T. (1992) *Genes Chromosom Cancer* 4, 1–15.
3. Harris, C. C. & Hollstein, M. (1993) *N Engl J Med* 329, 1318–27.
4. Greenblatt, M. S., Bennett, W. P., Hollstein, M. & Harris, C. C. (1994) *Cancer Res* 54, 4855–78.

5. Nigro, J. M., Baker, S. J., Preisinger, A. C., Jessup, J. M., Hostetter, R., Cleary, K, Bigner, S. H., Davidson, N., Baylin, S., Devilee, P. & et al. (1989) *Nature* 342, 705–8.
6. Baker, S. J., Preisinger, A. C., Jessup, J. M., Paraskeva, C., Markowitz, S., Wilson, J. K., Hamilton, S. & Vogelstein, B. (1990) *Cancer Res* 50, 7717–22.
7. Frebourg, T. & Friend, S. H. (1992) *J Clin Invest* 90, 1637–41.
8. Donehower, L. A. & Bradley, A. (1993) *Biochim Biophys Acta* 1155, 181–205.
9. Malkin, D. (1994) *Annu Rev Genet* 28, 443–65.
10. Michalovitz, D., Halevy, 0. & Oren, M. (1991) *J Cell Biochem* 45, 22–9.
11. Vogelstein, B. & Kinzier, K. W. (1992) *Cell* 70, 523–6.
12. Zambetti, G P. & Line, A. J. (1993) *Faseb J* 7, 855–65.
13. Hann, B. C. L., D. P. (1995) *Nature Genet.* 9, 221–222.
14. Rose, M. D., Winston F., and Hieter P. (1990) *Methods in yeast genetics: a laboratory course manual* (Cold Spring Harbor Laboratory, Cold Spring Harbor, N.Y.).
15. Ishioka, C., Frebourg, T., Yan, Y. X., Vidal, M., Friend, S. H., Schmidt, S. & Iggo, R. (1993) *Nature Genet* 5, 124–9.
16. Sikorski, R. S. & Hieter, P. (1989) *Genetics* 122, 19–27.
17. Devine, S. E. & Boeke, J. D. (1994) *Nucleic Acids Res* 22, 3765–72.
18. Sambrook, J., Fritsch, E. F., Maniatis, T. (1989) *Molecular cloning. A laboratory manual.* (Cold Spring Harbor Laboratory Press, Cold Spring Harbor, N.Y.).
19. Fields, S. & Song, O. (1989) *Nature* 340, 245–6.
20. Gyuris, J., Golemis, E., Chertkov, H. & Brent, R. (1993) *Cell* 75, 791–803.
21. Durfee, T., Becherer, K., Chen, P. L., Yeh, S. H., Yang, Y., Kilburn, A. E., Lee, W. H. & Elledge, S. J. (1993) *Genes Dev* 7, 555–69.
22. Wang, M. M. & Reed, R. R. (1993) *Nature* 364, 121–6.
23. Fields, S. & Jang, S. K. (1990) *Science* 249, 1046–9.
24. Boeke, 3. D., LaCroute, F. & Fink, G. R. (1984) *Mol Gen Genet* 17, 345–6.
25. el-Deiry, W. S., Kem, S. E., Pietenpol, J. A., Kinzier, K. W. & Vogelstein, B. (1992) *Nature Genet* 1, 45–9.
26. Herskowitz, I. (1987) *Nature* 329, 219–22.
27. Mazoyer, S., Lalle, P., Moyret-Lalle, C., Marcais, C., Schraub, S., Frappaz, D., Sobol, H. & Ozturk, M. (1994) *Oncogene* 9, 1237–9.
28. Gutierrez, M. I., Bhatia, K. G., Barreiro, C., Spangler, G., Schvartzmann, E., Muriel, F. S. & Magrath, I. T. (1994) *Hum Mol Genet* 3, 2247–8.
29. Cariello, N. F., Beroud, C. & Soussi, T. (1994) *Nucleic Acids Res* 22, 3549–50.
30. Hollstein, M., Rice, K., Greenblatt, M. S., Soussi, T., Fuchs, R., Sorlie, T., Hovig, E., Smith-Sorensen, B., Montesano, R. & Harris, C. C. (1994) *Nucleic Acids Res* 22, 3551–5.
31. Cho, Y., Gorina, S., Jeffrey, P. D. & Pavletich, N. P. (1994) *Science* 265, 346–55.
32. Friend, S. (1994) *Science* 265, 334–5.
33. Prives, C. (1994) *Cell* 78, 543–6.
34. Banks, L., Matashewski, G. & Crawford, L. (1986) *Eur J Biochem* 159, 529–34.
35. Gottlieb, T. M., and M. Oren. 1996. p53 in growth control and neoplasia. *Biochim Biophys Acta* 1287, no. 2–3:77–102.
36. Levine, A. J., J. Momand, and C. A. Finlay. 1991. The p53 tumour suppressor gene. [Review]. *Nature* 351, no. 6326:453–6.
37. Vogelstein, B., and K. W. Kinzier. 1994. Tumour-suppressor genes. X-rays strike p53 again [news; comment]. *Nature* 370, no. 6486:174–5.
38. Brachmann, R. K., M. Vidal, and J. D. Boeke. 1996. Dominant-negative p53 mutations selected in yeast hit cancer hot spots. *Proc Natl Acad Sci U S A* 93, no. 9:4091–5.
39. Hann, B. C. L., D. P. 1995. The dominating effect of mutant p53. *Nature Genetics* 9, no. March:221–222.
40. Ko, L. J., and C. Prives. 1996. p53: puzzle and paradigm. *Genes Dev* 10, no. 9:1054–72.
41. Lowe, S. W., H. E. Ruley, T. Jacks, and D. E. Housman. 1993. p53-dependent apoptosis modulates the cytotoxicity of anticancer agents. *Cell* 74, no. 6:957–67.
42. Lowe, S. W. 1995. Cancer therapy and p53. *Curr Opin Oncol* 7, no. 6:547–53.
43. Kinzler, K. W., and B. Vogelstein. 1994. Cancer therapy meets p53 [see comments]. *N Engl J Med* 331, no. 1:49–50.
44. Chang, F., S. Syijanen, and K. Syrjanen. 1995. Implications of the p53 tumor-suppressor gene in clinical oncology [see comments]. *J Clin Oncol* 13, no. 4:1009–22.
45. Anderson, M. E., and P. Tegtmeyer. 1995. Giant leap for p53, small step for drug design. *Bioessays* 17, no. 1:3–7.
46. Harris, C. C. 1996. Structure and function of the p53 tumor suppressor gene: clues for rational cancer therapeutic strategies. *Journal of the National Cancer Institute* 88, no. 20:1442–1454.
47. Milner, J. 1995. DNA damage, p53 and anticancer therapies. *Nature Medicine* 1, no. 9:879–80.
48. Gibbs, J. B., and A. Oliff. 1994. Pharmaceutical research in molecular oncology. *Cell* 79, no. 2:193–8.
49. McNabb, D. S., and L. Guarente. 1996. Genetic and biochemical probes for protein-protein interactions. *Current Opinion in Biotechnology* 7:554–559.
50. Vidal, M., R. K. Brachmann, A. Fattaey, E. Harlow, and J. D. Boeke. 1996. Reverse two-hybrid and one-hybrid systems to detect dissociation of protein-protein and DNA-protein interactions. *Proc. Natl. Acad. Sci. USA* 93:10315–10320.
51. Robzyk, K., and Y. Kassir. 1992. A simple and highly efficient procedure for rescuing autonomous plasmids from yeast. *Nucleic Acids Res* 20, no. 14:3790.
52. Sikorski, R. S., and P. Hieter. 1989. A system of shuttle vectors and yeast host strains designed for efficient manipulation of DNA in *Saccharomyces cerevisiae*. *Genetics* 122, no. 1:19–27.
53. Higuchi, R., B. Krummel, and R. K. Saiki. 1988. A general method of in vitro preparation and specific mutagenesis of DNA fragments: study of protein and DNA interactions. *Nucleic Acids Res* 16, no. 15:7351–67.
54. Cariello, N. F., L. Cui, C. Beroud, and T. Soussi. 1994. Database and software for the analysis of mutations in the human p53 gene. *Cancer Res* 54, no. 16:4454–60.
55. Wieczorek A. M., J. L. Waterman, M. J. Waterman, and T. D. Halazonetis. 1996.
    Structure-based rescue of common tumor-derived p53 mutants. *Nature Medicine* 2, no. 10:1143–1146.
56. Freeman, J., S. Schmidt, E. Scharer, and R. Iggo. 1994. Mutation of conserved domain II alters the sequence specificity of DNA binding by the p53 protein. *Embo J* 13, no. 22:5393–400.
57. Waterman, M. J., J. L. Waterman, and T. D. Halazonetis. 1996. An engineered four-stranded coiled coil substitutes for the teramerization domain of wild-type p53 and alleviates transdominant inhibition by tumor-derived p53 mutants. *Cancer Res* 56, no. 1:158–63.

What is claimed is:

1. A method for identifying yeast cells which carry mutations in a human p53 gene, wherein said mutations suppress the phenotype of dominant-negative p53 mutations, comprising the step of:
    determining the phenotype of a cell comprising a nucleic acid encoding human p53 which comprises a dominant negative mutation which has been further mutagenized to induce a suppressor mutation, if the phenotype of the cell is that of a cell carrying a wild-type p53 then the cell is a candidate cell for carrying a human p53 suppressor mutation which suppresses the phenotype of the dominant-negative mutation.

2. The method of claim 1 wherein the phenotype is determined by observing expression of a gene which is dependent on p53 for expression.

3. The method of claim 2 wherein the p53dependent gene is selected from the group consisting of $p_{21}^{WAF1}$, GADD45, IGF-BP3, and bax.

4. The method of claim 2 wherein the p53dependent gene is a reporter gene under the control of a p53 responsive transcription element.

5. The method of claim 1 wherein he dominant-negative mutation is selected from the group consisting of: V143A, R175H, G245D, G245S, R248W, R249S, R248Q, R273H, R273C, R282W, and R273P.

6. The method of claim 1 wherein the nucleic acid encoding human p53 was mutagenized using PCR-generated fragments to recombine with a gapped p53-encoding molecule.

7. The method of claim 1 wherein the mutagenized nucleic acid encoding human p53 comprises an oligomerization domain of human p53.

8. A method for identifying yeast cells which carry mutations in a human p53 gene, wherein said mutations suppress the phenotype of dominant negative p53 mutations, comprising the steps of:
    mutagenizing a nucleic acid comprising a dominant-negative allele of human p53;
    supplying the nucleic acid which has been mutagenized to a cell;
    determining the phenotype of the cell; if the phenotype is that of a cell carrying a wild-type p53, then the cell is a candidate cell for carrying a human p53 suppressor mutation which suppresses the phenotype of the dominant-negative mutation.

9. A method for identifying yeast cells which carry mutations in a human p53 gene, wherein said mutations suppress the phenotype of dominant-negative p53 mutations, comprising the steps of:
    introducing a mutagenized nucleic acid encoding human p53 into a cell comprising a dominant-negative p53 expression construct;
    determining the phenotype of the cell; if the phenotype is that of a cell carrying a wild-type p53, then the cell is a candidate cell for carrying a human p53 suppressor mutation which suppresses the phenotype of the dominant-negative mutation.

10. The method of claim 9 wherein the nucleic acid comprises an oligomerization domain of human p53.

11. A method for identifying yeast cells which carry mutations in a human p53 gene, wherein said mutations suppress the phenotype of dominant-negative p53 mutations, comprising the steps of:
    introducing a mutegenized nucleic acid encoding human p53 into cells comprising (a) a dominant-negative p53 expression construct and (b) a selectable reporter gene operably linked to a DNA sequence to which human p53 specifically binds;
    selecting a cell expressing the reporter gene, wherein said cell is a candidate cell for carrying a human p53 suppressor mutation which suppresses the phenotype of the dominant-negative p53.

12. The method of claim 8 wherein the nucleic acid which has been mutagenized comprises an oligomerization domain of human p53.

13. The method of claim 11 wherein the mutagenized nucleic acid comprises an oligomerization domain of human p53.

* * * * *